US011060152B2

(12) United States Patent
Roperch

(10) Patent No.: US 11,060,152 B2
(45) Date of Patent: Jul. 13, 2021

(54) METHODS FOR THE SURVEILLANCE, DIAGNOSIS AND SCREENING OF BLADDER CANCER

(71) Applicant: ONCODIAG, Paris (FR)

(72) Inventor: Jean-Pierre Roperch, Lommoye (FR)

(73) Assignee: ONCODIAG, Paris (FR)

( * ) Notice: Subject to any disclaimer, the term of this patent is extended or adjusted under 35 U.S.C. 154(b) by 0 days.

(21) Appl. No.: 16/173,189

(22) Filed: Oct. 29, 2018

(65) Prior Publication Data

US 2019/0062849 A1 Feb. 28, 2019

Related U.S. Application Data

(63) Continuation of application No. 15/037,073, filed as application No. PCT/EP2014/074892 on Nov. 18, 2014, now abandoned.

(30) Foreign Application Priority Data

Nov. 19, 2013 (EP) .................................... 13306580

(51) Int. Cl.
*C07H 21/04* (2006.01)
*C12Q 1/68* (2018.01)
*C12Q 1/6886* (2018.01)

(52) U.S. Cl.
CPC ...... *C12Q 1/6886* (2013.01); *C12Q 2600/118* (2013.01); *C12Q 2600/154* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 7,135,311 | B1 * | 11/2006 | David | C12Q 1/6886 435/91.2 |
| 2012/0252019 | A1 * | 10/2012 | Shuber | G01N 33/57407 435/6.11 |

OTHER PUBLICATIONS

Angulo et al. (E. Urology, Supplements, vol. 11, No. 1, e167, Feb. 2012) (Year: 2012).*
Stubendorff et al. (J. of Urology, vol. 189, No. 4S, May 6, 2013) (Year: 2013).*
Fernandez et al. ( Genome Research, vol. 22, pp. 407-419, 2012) (Year: 2012).*

* cited by examiner

*Primary Examiner* — Jeanine A Goldberg
(74) *Attorney, Agent, or Firm* — W&C IP

(57) ABSTRACT

A method of diagnosing or predicting a bladder cancer, or a risk of a developing a bladder cancer in a subject is provided, which method includes the detection of specific mutations in the FGFR3 gene in a first biological sample; and the measure of the degree of methylation of target genes in a biological sample obtained from the subject in a second biological sample.

6 Claims, 4 Drawing Sheets

Figure 1:
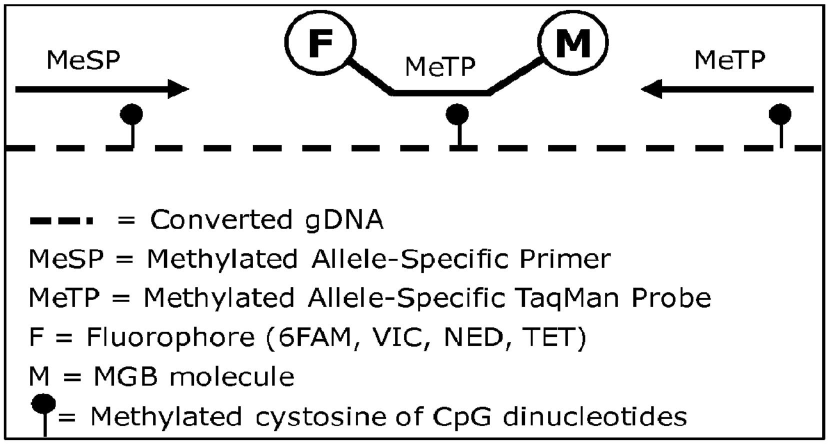

Specification includes a Sequence Listing.

METHODS FOR THE SURVEILLANCE, DIAGNOSIS AND SCREENING OF BLADDER CANCER

FIELD OF THE INVENTION

The present invention relates to a method for prognosis, diagnosis and screening of bladder cancer. The invention is highly useful for the surveillance of recurrences and follow-up of patient suffering or which have suffered from bladder cancer.

BACKGROUND OF THE INVENTION

Bladder cancer is the $5^{th}$ most common cancer diagnosis worldwide, with more than 330,000 new cases each year and more than 130,000 deaths per year, with an estimated male:female ratio of 3.0:1.0. Bladder cancer is a disease of older individuals with greater than 90% of diagnoses in patients more than 55 years of age; although uncommon, bladder cancer can occur in young adults and even in children. At any point in time 2.7 million people have a history of urinary bladder cancer. Of newly, diagnosed bladder cancer cases, approximately 70%-80% will present at an early stage, but 70% of these will recur and 10%-30% will progress to advanced disease. For the majority of patients who present non-muscle invasive in early stage (called "superficial") disease, management generally includes endoscopic resection, intravesical therapies, and surveillance cystoscopy. Collectively, this approach aims to minimize the risks of recurrence and progression. Conversely, for those patients with advanced (muscle invasive) disease, strategies are commonly multidisciplinary and target both local (radical cystectomy, radiation therapy) and systemic (chemotherapy) disease. In recent decades the overall incidence of bladder cancer has appeared to be rising and this may be due to the latent effects of tobacco abuse and industrial carcinogens.

In the case of bladder cancer, development of accurate and noninvasive bladder tumor markers could be important in screening, initial diagnosis, surveillance for recurrence, detection of early progression, and prediction of prognosis, without increasing the frequency of invasive and relatively costly current diagnostic procedures. A bladder screening program should be feasible in addition to promoting early detection. However, because of the low prevalence of bladder cancer in the general population (0.001%) and in people >50 years of age (0.67% to 1.13%), screening the whole population for bladder cancer would raise the possibility of too many false-positive results and would not be cost-effective. Bladder cancer screening may be cost-effective among individuals who are at a higher risk for this cancer (smokers, occupational exposure to aromatic amines, schistosomias). The risk for bladder cancer is even higher when smoking is combined with other known bladder carcinogens or genetic polymorphisms.

Bladder cancer may be diagnosed incidentally or because of symptoms. The main symptom of bladder cancer is hematuria. Urine cytology is not a laboratory test; it is a pathologist's interpretation of the morphologic features of urothelial cells. Urinary specimens do not always contain a representative sample of the bladder and may not contain tumor cells, even when a tumor is present. The sensitivity and specificity of urine cytology is low for detecting low-grade tumors. The clinical diagnosis of bladder cancer is usually made by flexible or rigid cystoscopy. Cystoscopy is considered as the gold standard for bladder cancer diagnosis and offers the capability to find and remove small lesions, but it is associated with high cost, substantial patient discomfort, and variable sensitivity.

Because of the frequency of recurrence, the standard of care for bladder cancer surveillance consists of periodic cystoscopies after tumor resection. Hematuria screening can detect not only bladder cancer, but also other urologic malignancies and benign diseases (benign prostatic hyperplasia) that need medical attention can be detected early, and many other conditions that produce blood in the urinary tract. Hematuria associated with bladder cancer is also independent of tumor grade.

Currently, no tumor markers tests can be recommended for use in the diagnosis and clinical management of bladder cancer with an acceptable efficiency. The few available methods determine bladder cancer prognosis and select patients for appropriate therapy upon parameters such as tumor size, tumor grade, the age of the patient.

However, the predictive accuracy of those diagnosis/staging strategies remains limited, as they may not reflect the complexity of molecular events driving bladder cancer onset and progression.

Thus, there is still an unfulfilled need for a method for accurately diagnosing bladder cancer which would distinguish tumors associated with good prognosis including low probability of metastasis, late disease progression, decreased disease recurrence or increased patient survival, from the others.

Using such method, the practitioner would be able to accurately predict the patient's prognosis and would be able to effectively target the individuals who would most likely benefit from therapy or who need a more intensive monitoring.

SUMMARY OF THE INVENTION

The inventors have established that measuring the combination of two assays based on one hand on the identification of specific mutations of FGFR3 and on the other hand the measure of the degree of methylation of specific marker would provide for an accurate prediction and/or detection of bladder cancer.

The invention thus relates to a method for the surveillance, diagnosis and screening of a bladder cancer, or a risk of a developing a bladder cancer in a subject, which method comprises:

a) a step of detecting a mutation in the FGFR3 gene in a first biological sample; and
b) a step of measuring the degree of methylation of at least one gene selected from the group consisting of SEPTIN 9, SLIT 2, TWIST 1, HS3ST2 and fragments or variants thereof in a second biological sample obtained from said subject, wherein said step a) is performed by:

detecting a mutation selected from the group consisting of mutations 742C→T, 746C→G, 1114G→T, and 1124A→G by reference to the nucleotide numbers of SEQ ID No 1; or detecting a mutation in the group consisting of mutations Arg248Cys, Ser249Cys, Gly372Cys, and Tyr375Cys, by reference to the amino acid numbers of SEQ ID No 2.

Preferably, said first and second biological sample is an urine sample. Typically, both step a) and b) are performed on the same urine sample.

Preferably, said method comprise a further step b') after step b) of comparing the degree of methylation measured in step b) to a threshold value, wherein said threshold value distinguishes between patient suffering or at risk of developing a bladder cancer and patient who do not suffer from bladder cancer.

Preferably, the presence of said mutation in the FGFR3 gene, and the comparison of the methylation degree of at least one gene selected from the group consisting of SEPTIN 9, SLIT 2, TWIST 1. HS3ST2 and fragment or variant thereof to a threshold value, are indicative of a bladder cancer or of a risk of developing a bladder cancer.

Preferably, step a) of the method of the invention further comprises the detection of a mutation in TERT gene, said detection being performed by:

- detecting a mutation selected from the group consisting of mutations 77C→T and 99C→T by reference to the nucleotide numbers of SEQ ID No 32.

Preferably, step b) of the method of the invention consists in:

- measuring the degree of methylation of a fragment of SEPTIN 9, as depicted in SEQ ID No 3;
- measuring the degree of methylation of a fragment of SLIT 2, as depicted in SEQ ID No 4;
- measuring the degree of methylation of a fragment of TWIST 1, as depicted in SEQ ID No 5; and
- measuring the degree of methylation of a fragment of HS3ST2, as depicted in SEQ ID No 6.

Preferably, step b) of the method of the invention further comprises the measure of the degree of methylation of DDR1 gene and fragments or variants thereof. Preferably, said fragment is depicted in SEQ ID No 7.

Preferably, said first and second biological samples are urine.

Preferably, step a) of the method of the invention is performed by allele specific PCR (AS-PCR). Typically, step a) is performed using the primers as depicted in SEQ ID No 8 to 13.

Preferably, step b) of the method of the invention is performed by quantitative real-time multiplex methylation specific polymerase chain reaction (Qm-PCR). Typically, said step b) further comprises a step of measuring the degree of methylation of a housekeeping gene, which is typically selected among albumin, β-Actin and β-Globin, preferably the albumin gene or a fragment or variant thereof.

DETAILED DESCRIPTION OF THE INVENTION

The inventors showed that the combination of two assays, respectively based:

- on the detection of specific mutations of FGRF3; and
- on the quantification of degree of methylation of target genes, provides promising strategy for detection of bladder cancer, with an extremely high sensitivity and specificity.

Thus, accordingly, in a first aspect, the invention relates to a method for the surveillance, diagnosis and screening of a bladder cancer, or a risk of a developing a bladder cancer in a subject, wherein said method comprises:

- a) a step of detecting a mutation in the FGFR3 gene in a first biological sample, and
- b) a step of measuring the degree of methylation of at least one gene selected from the group consisting of SEPTIN 9, SLIT 2, TWIST 1, HS3ST2 and fragments or variants thereof in a second biological sample obtained from said subject, wherein said step a) is performed by:

- detecting a mutation selected from the group consisting of mutations 742C→T, 746C→G, 1114G→T, and 1124A→G by reference to the nucleotide numbers of SEQ ID No 1; or
- detecting a mutation in the group consisting of mutations Arg248Cys, Ser249Cys, Gly372Cys, and Tyr375Cys, by reference to the amino acid numbers of SEQ ID No 2.

Preferably, wherein said method comprises a further step b') after step b) of comparing the degree of methylation measured in step b) to a threshold value, wherein said threshold value distinguishes between a patient suffering or at risk of developing a bladder cancer and a patient who does not suffer from bladder cancer.

The method of the invention is thus a method which predicts efficiently bladder cancer prognosis a patient. Said method thus can be readily adapted for bladder cancer management as well as patient allocation in clinical trials with new drugs. Indeed, said method allows:

- surveillance of recurrences, i.e. the follow-up of patients already diagnosed as suffering of bladder cancer,
- initial diagnosis of bladder cancer in a patient,
- screening, i.e. identification of a population at risk of developing a bladder cancer.

As used herein, population at risk of developing a bladder cancer includes:

- individuals who smoke,
- individuals exposed to various chemical, especially in sites of refinery or in oil and gas industry,
- individuals suffering from chronic urinary infection,
- individuals suffering from permanent bladder infection such as schistosomiasis The method provides crucial information to the practitioner in order for him to determine the appropriate therapeutic strategy to deploy and/or decide whether the patient should be treated by adjuvant therapy, i.e. additional therapy.

Definition

The term “FGRF3” refers to the gene of fibroblast growth factor receptor 3. Said gene encodes a member of the fibroblast growth factor receptor (FGFR) family, with its amino acid sequence being highly conserved between members and among divergent species. FGFR family members differ from one another in their ligand affinities and tissue distribution. A full-length representative protein would consist of an extracellular region, composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. This particular family member binds acidic and basic fibroblast growth hormone and plays a role in bone development and maintenance. Mutations in this gene lead to craniosynostosis and multiple types of skeletal dysplasia. Three alternatively spliced transcript variants that encode different protein isoforms have been described.

The terms “mutant” and “mutation” mean any detectable change in genetic material, e.g. DNA, RNA, cDNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. Generally a mutation is identified in a subject by comparing the sequence of a nucleic acid or polypeptide expressed by said subject with the corresponding nucleic acid or polypeptide expressed in a control population. A mutation in the genetic material may also be "silent", i.e. the mutation does not result in an alteration of the amino acid sequence of the expression product.

In the context of the instant application, mutations identified in FGFR3 gene are designated pursuant to the nomenclature of Dunnen and Antonarakis (2000). As defined by Dunnen and Antonarakis at the nucleic acid level, substitutions are designated by ">", e.g. "1463T>C" denotes that at nucleotide 1463 of the reference sequence a T is changed to a C. When the full-length genomic sequence is known, the mutation is best designated by the nucleotide number of the genomic references.

As used herein, the expression "targeted mutations" refers to specific mutations on the FGFR3 gene, defined as follows:
- mutations 742C→T, 746C→G, 1114G→T, and 1124A→G by reference to the nucleotide numbers of SEQ ID No 1, or
- mutations Arg248Cys, Ser249Cys. Gly372Cys, and Tyr375Cys, by reference to the amino acid numbers of SEQ ID No 2.

As used herein, the term "subject" refers to an individual with symptoms of and/or suspected of having bladder cancer.

The term "cancer" or "tumor", as used herein, refers to the presence of cells possessing characteristics typical of cancer-causing cells, such as uncontrolled proliferation, immortality, metastatic potential, rapid growth and proliferation rate, and certain characteristic morphological features. Preferably the cancer is a bladder cancer.

As used herein, the term "patient" denotes a mammal, such as a rodent, a feline, a canine, and a primate. Preferably, a patient according to the invention is a human.

The term "adjuvant therapy", as used herein, refers to any type of treatment of cancer given as additional treatment, usually after surgical resection of the primary tumor, in a patient affected with a cancer that is at risk of metastasizing and/or likely to recur. The aim of such an adjuvant treatment is to improve the prognosis. Adjuvant therapies comprise radiotherapy and therapy, preferably systemic therapy, such as hormone therapy, chemotherapy, immunotherapy and monoclonal antibody therapy.

As used herein, the term "gene" refers to a nucleic acid fragment that expresses a specific protein, including regulatory sequences preceding (5' non-coding sequences) and following (3' non-coding sequences) the coding sequence.

As used herein, the expression "genes of Interest" refers to SEPTIN 9, SLIT 2, TWIST 1, HS3ST2 genes and fragments or variants thereof.

As used herein, the term "gene expression level" or "the expression level of a gene" refers to an amount or a concentration of a transcription product, for instance mRNA, or of a translation product, for instance a protein or polypeptide. Typically, a level of mRNA expression can be expressed in units such as transcripts per cell or nanograms per microgram of tissue. A level of a polypeptide can be expressed as nanograms per microgram of tissue or nanograms per milliliter of a culture medium, for example. Alternatively, relative units can be employed to describe an expression level.

As used herein, the expression "mRNA transcript" refers to the product resulting from RNA polymerase-catalyzed transcription of a DNA sequence without introns and that can be translated into polypeptides by the cell.

As used herein, the term "biological sample" as used herein refers to any biological sample obtained for the purpose of evaluation in vitro. Typically, said biological sample can be obtained from solid tissues and tumor tissues. Examples of additional test samples include urine, blood, serum, plasma, nipple aspirate fluid, saliva, synovial fluid and cephalorachidian liquid (CRL). Preferably, said biological sample is urine. Typically, urine may comprise tumor derived material such as tumor cells or tumor relapsed proteins and/or nucleic acids. Typically, said first and second biological samples are the same or different biological samples.

As used herein, the expression of "measuring the expression level of a gene" encompasses the step of measuring the quantity of a transcription product, preferably mRNA obtained through transcription of said gene, and/or the step of measuring the quantity of translation product, preferably the protein obtained through translation of said gene. Preferably, the step of measuring the expression of a gene refers to the step of measuring the quantity of mRNA obtained through transcription of said gene. Typically, the step a) of measuring the level of gene expression of said gene(s) may be performed according to the routine techniques, well known of the person skilled in the art.

"Screening for bladder cancer" means detection of a predisposition to develop bladder cancer, as well as detection of bladder cancer already present in a subject.

"Methylation" means addition of a methyl group on carbon 5 of a cytosine in a CpG dinucleotide. These dinucleotides do not occur frequently in the structure of DNA, except in the CpG "islands". These islands are typically represented at the level of the promoter region of the genes. Thus, when we talk of methylation of a gene, we are referring to methylation of the promoter region of said gene. The presence of a methyl group in a precise site prevents interaction between the gene and the transcription factors. Typically, the methyl groups prevent the transcription factors attaching to the amplification site and to the promoter, and prevent RNA polymerase attaching to the initiation site. Thus, methylation of the promoter region leads to repression of DNA transcription.

The expression "methylation of a gene" encompasses methylation of the CpG islands of the nucleotide sequence of the gene but also methylation of the nucleotide sequences of the promoter of the gene to which said expression is applied.

"Fragment of a gene" means a sequence of said gene with a length of at least 50 base pairs, preferably with a length of between 60 and 120 base pairs.

Detection of Specific Mutations in the FGFR3 Gene

The method of the invention comprises a step a) of detecting a mutation in the FGFR3 gene in a first biological sample wherein said step a) is performed by:
- detecting a mutation selected from the group consisting of mutations 742C→T, 746C→G, 1114G→T, and 1124A→G by reference to the nucleotide numbers of SEQ ID No 1; or
- detecting a mutation in the group consisting of mutations Arg248Cys, Ser249Cys, Gly372Cys, and Tyr375Cys, by reference to the amino acid numbers of SEQ ID No 2.

Preferably, said step b) is a step of measuring the degree of methylation of at least two genes, preferably at least three genes selected from the group consisting of SEPTIN 9, SLIT 2, TWIST 1, HS3ST2 and fragments or variants thereof in a second biological sample obtained from said subject.

More preferably, said step b) is a step of measuring the degree of methylation of all the genes SEPTIN 9, SLIT 2, TWIST 1, HS3ST2 and fragments or variants thereof in a second biological sample obtained from said subject.

Preferably, said first and biological sample are the same biological sample. Preferably, step a) is a step of detecting a mutation selected from the group consisting of 746C→G, 1114 G→T, and 1124A→G by reference to the nucleotide numbers of SEQ ID No 1 or mutations Ser249Cys, Gly372Cys, and Tyr375Cys, by reference to the amino acid numbers of SEQ ID No 2.

Typically, the detection of the target mutation can be performed on DNA sequences, on mRNA transcripts, or on protein sequences. More preferably, the detection of the target mutation can be performed on DNA sequences which were treated with bisulfite.

Preferably, the mutation of FGFR3 to detect is selected from the group consisting of mutations:

742C→T,

746C→G,

1114G→T, and

1124A→G, by reference to the nucleotides numbers of SEQ ID No 1, which refers to the DNA sequence encoding for the protein FGFR3. SEQ ID No 1 is a fragment of the sequence available online under the accession number NM_ 001163213.1 (NCBI Reference Sequence). SEQ ID No 1 encodes for the amino acid sequence depicted in SEQ ID No 2.

In SEQ ID No 1, the nucleotide in position 742 is a cytosine. The mutation 742C→T consists of the substitution of said cytosine in position 742 by a thymine. Said mutation leads to a protein which comprises a cysteine in position 248 instead of an arginine, by reference to SEQ ID No 1.

In SEQ ID No 1, the nucleotide in position 746 is a cytosine. The mutation 746C→G consists of the substitution of said cytosine in position 746 by a guanine. Said mutation leads to a protein having a cysteine in position 248 instead of a serine by reference to SEQ ID No 1.

In SEQ ID No 1, the nucleotide in position 1114 is a guanine. The mutation 1114G→T consists of a substitution of said guanine by a thymine. Said mutation leads to a protein having cysteine in position 372 instead of a glycine by reference to SEQ ID No 1.

In SEQ ID No 1, the nucleotide in position 1124 is an adenine. The mutation 1124A→G consists of a substitution of said adenine by a guanine. Said mutation leads to a protein having a cysteine in position 375 instead of a tyrosine by reference to SEQ ID No 1.

According to a first embodiment, said mutation may be detected by analyzing a FGFR3 nucleic acid molecule.

In the context of the invention, "FGFR3 nucleic acid molecules" include mRNA, genomic DNA and cDNA derived from mRNA. FGFR3 mutations may be detected in a RNA or DNA sample, preferably after amplification.

DNA or RNA can be single stranded or double stranded. These may be utilized for detection by amplification and/or hybridization with a probe, for instance. The nucleic acid sample may be obtained from any cell source or tissue biopsy. Non-limiting examples of cell sources available include without limitation blood cells, buccal cells, epithelial cells, fibroblasts, or any cells present in a tissue obtained by biopsy. Cells may also be obtained from body fluids, such as urine, blood, plasma, serum, lymph, etc. Preferably, cells are obtained from urine samples.

DNA may be extracted using any methods known in the art, such as described in Sambrook et al., 1989. RNA may also be isolated, for instance from tissue biopsy, using standard methods well known to the one skilled in the art such as guanidium thiocyanate-phenol-chloroform extraction.

The isolated RNA may be subjected to coupled reverse transcription and amplification, such as reverse transcription and amplification by polymerase chain reaction (RT-PCR), using specific oligonucleotide primers that are specific for a mutated site or that enable amplification of a region containing the mutated site.

Typically, conditions for primer annealing may be chosen to ensure specific reverse transcription (where appropriate) and amplification; so that the appearance of an amplification product be a diagnostic of the presence of a particular FGFR3 mutation. Otherwise, RNA may be reverse-transcribed and amplified, or DNA may be amplified, after which a mutated site may be detected in the amplified sequence by hybridization with a suitable probe or by direct sequencing, or any other appropriate method known in the art. For instance, a cDNA obtained from RNA may be cloned and sequenced to identify a mutation in FGFR3 sequence.

Numerous strategies for genotype analysis are available (Antonarakis et al., 1989; Cooper et al., 1991; Grompe, 1993). Briefly, the nucleic acid molecule may be tested for the presence or absence of a restriction site. When a base substitution mutation creates or abolishes the recognition site of a restriction enzyme, this allows a simple direct PCR test for the mutation. Further strategies include, but are not limited to, direct sequencing, restriction fragment length polymorphism (RFLP) analysis; hybridization with allele-specific oligonucleotides (ASO) that are short synthetic probes which hybridize only to a perfectly matched sequence under suitably stringent hybridization conditions; allele-specific PCR; PCR using mutagenic primers; ligase-PCR. HOT cleavage; denaturing gradient gel electrophoresis (DGGE), temperature denaturing gradient gel electrophoresis (TGGE), single-stranded conformational polymorphism (SSCP) and denaturing high performance liquid chromatography (Kuklin et al., 1997). Direct sequencing may also be accomplished by any method, including without limitation chemical sequencing, using the Maxam-Gilbert method; by enzymatic sequencing, using the Sanger method; mass spectrometry sequencing; sequencing using a chip-based technology; and real-time quantitative PCR. Preferably, DNA from a subject is first subjected to amplification by polymerase chain reaction (PCR) using specific amplification primers.

However, several other methods are available, allowing DNA to be studied independently of PCR, such as the rolling circle amplification (RCA), the InvaderTMassay, or oligonucleotide ligation assay (OLA). OLA may be used for revealing base substitution mutations. According to this method, two oligonucleotides are constructed that hybridize to adjacent sequences in the target nucleic acid, with the join sited at the position of the mutation. DNA ligase will covalently join the two oligonucleotides only if they are perfectly hybridized.

Preferably, step a) of the method of the invention can be carried out by allele specific Polymerase Chain Reaction (AS-PCR).

As used herein. "Allele-specific polymerase chain reaction" (AS-PCR) refers to a specific embodiment of the polymerase chain reaction that permits the direct detection of any point mutation in human DNA by analyzing the PCR products in an ethidium bromide-stained agarose or polyacrylamide gel. AS-PCR works because an oligonucleotide primer that forms a 3' mismatch with the DNA template will be refractory to primer extension by *Thermus aquaticus* DNA polymerase. Therefore, oligonucleotide primers specific for all known alleles can be synthesized and used to detect the alleles in DNAs of unknown genotype. synthesized using LNA have greater thermal stability than conventional DNA or RNA and therefore form a stronger bond with the complementary sequence. Typically, when detecting the FGFR3 mutations, one can use the forward and reverse primers as disclosed in the table 1.

TABLE 1

Primers used for detecting the targeted mutations on the FGFR3 gene

| Mutation to detect | Name of the primer | SEQ ID No | Core Sequence | Used Sequence |
|---|---|---|---|---|
| 742C→T | Forward F1 | 8 | 5' CAG TGG CGG TGG TGG TGA GG 3' | 5' 6FAM- CAC TGG CGG TGG TGG TGA GG 3' (SEQ ID No 8 tagged in 5' with FAM) |
| | Reverse R2 | 9 | 5' ATG GGC CGG TGC GGG GAG **CA** 3' | 5' ATG GGC CGG TGC GGG GAG C* **A** 3' (SEQ ID No 9 with cytosine in position 19 modified by LNA technology) |
| 746 C→G | Forward F1 | 8 | 5' CAG TGG CGG TGG TGG TGA GG 3' | 5' 6FAM- CAG TGG CGG TGG TGG TGA GG 3' (SEQ ID No 8 tagged in 5' with FAM) |
| | Reverse R1 | 10 | 5' CAG GAT GGG CCG GTG CGG **GC** 3' | 5' CAG CAT GGG CCG GTG CGG G* **C** 3' (SEQ ID No 10 with guanine in position 19 modified by LNA teclmology) |
| 1114 G→T | Forward F2 | 11 | 5' ATG TCT 'TTG CAG CCG AGG AGG AG 3' | 5' HEX- ATG TCT TTG CAG CCG AGG AGG AG 3' (SEQ ID No 11 tagged in 5' with HEX) |
| | Reverse R3 | 12 | 5' AGC TGA GGA TGC CTG CAT ACA CAC TGC **A** 3' | 5' AGC TGA GGA TGC CTG CAT ACA CAC TGC* **A** 3' (SEQ ID No 12 with cytosine in position 27 modified by LNA technology) |
| 1124 A→G | ForwardF2 | 11 | 5' ATG TCT TTG CAG CCG AGG AGG AG 3' | 5' HEX- ATG TCT TTG CAG CCG AGG AGG AG 3' (SEQ ID No 11 tagged in 5' with HEX) |
| | Reverse R4 | 13 | 5' ACC CCG TAG CTG ACC ATG CCT GCT **C** 3' | 5' ACC CCG TAG CTG AGG ATG CCT GCT **C*** 3' (SEQ ID No 13 with cytosine in position 25 modified by LNA technology) |

Basically, the general principle underlying the AS-PCR techniques is thus to design a mutation-specific primer that produces the preferential amplification of a specific mutant allele.

For implementing the AS-PCR method, one can use the primers defined as below:

- one forward primer (SEQ ID No 8 and 11) tagged in 5' with a specific fluorescent dye such as 6FAM, HEX, and TET and
- one reverse primer (SEQ ID No 9, 10, 12 and 13) presenting a nucleotide modified in 3' by Locked Nucleic Acid technology.

As used herein, the expression "nucleotide modified by Locked Nucleic Acid technology" or "nucleotide modifies by LNA" refers to oligonucleotides which are ideal when studying short or very similar sequences. The high affinity of an LNA oligonucleotide to its complementary sequence results in dramatically improved specificity compared to traditional DNA oligonucleotide and used to distinguish between sequences differing by a single nucleotide, which can be critical for the success of many experiments. Indeed, when used with any standard bases (A, C, G, T, or U), probes The nucleotides noted with an asterisk in table 1 are modified by LNA technology.

SEQ ID No 8 to 13, depicted in the listing sequence enclosed are tagged in 5' with a specific fluorescent dye such as 6FAM, HEX, and TET or present a nucleotide modified in 3' by Locked Nucleic Acid technology, as shown in table 1.

Typically, when implementing the AS-PCR in step a) of the method of the invention, one may use an internal control, such as a housekeeping gene.

Preferably said housekeeping gene is selected from the group consisting of albumin, β-Actin and β-Globin or fragments and variants thereof. Preferably, said housekeeping gene is β-Globin or fragments and variants thereof. More preferably, the internal control is a fragment of a housekeeping gene, more preferably a fragment of β-Globin. Typically, said fragment is the nucleotide sequence depicted in SEQ ID No 31.

For this purpose, one can also use the following primers:

```
Forward FGLO:
                                        (SEQ ID No 14)
5' HEX- CCT TTG GGG ATC TGT CCA CTC CTG A 3';
and

Reverse RGLO:
                                        (SEQ ID No 15)
5' GTT GTC CAG GTG AGC CAG GCC AT 3'
```

Preferably, step a) of the method of the invention can be carried out by allele specific Polymerase Chain Reaction (AS-PCR) using two PCRs as follows:

PCR1 which detect the mutations 742C→T and 1114G→T by reference to the nucleotide numbers of SEQ ID No 1, and the β-globin;

PCR2 which detects the 7422C→G and 1124A→G by reference to the nucleotide numbers of SEQ ID No 1, and the β-globin.

According to a second embodiment said mutation in the FGFR3 gene may be detected at the protein level. Accordingly, a mutation of FGFR according to the invention is preferably selected from the group consisting of mutations Arg248Cys. Ser249Cys, Gly372Cys and Tyr375Cys, and, by reference to the amino acid numbers of SEQ ID No 2. Said mutation may be detected according to any appropriate method known in the art. In particular a sample, such as a tissue biopsy, obtained from a subject may be contacted with antibodies specific of the mutated form of FGFR3, i.e. antibodies that are capable of distinguishing between a mutated form of FGFR3 and the wild-type protein (or any other protein), to determine the presence or absence of a FGFR3 specified by the antibody. Antibodies that specifically recognize a mutated FGFR3 also make part of the invention. The antibodies are specific of mutated FGFR3 that is to say they do not cross-react with the wild-type FGFR3.

The antibodies of the present invention may be monoclonal or polyclonal antibodies, single chain or double chain, chimeric antibodies, humanized antibodies, or portions of an immunoglobulin molecule, including those portions known in the art as antigen binding fragments Fab, Fab', F(ab')2 and F(v). They can also be immunoconjugated, e.g. with a toxin, or labelled antibodies.

Whereas polyclonal antibodies may be used, monoclonal antibodies are preferred for they are more reproducible in the long run. Procedures for raising "polyclonal antibodies" are also well known. Polyclonal antibodies can be obtained from serum of an animal immunized against the appropriate antigen, which may be produced by genetic engineering for example according to standard methods well-known by one skilled in the art. Typically, such antibodies can be raised by administering mutated FGFR3 subcutaneously to New Zealand white rabbits which have first been bled to obtain pre-immune serum. The antigens can be injected at a total volume of 100 μl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al. (1988) which is hereby incorporated in the references.

A "monoclonal antibody" in its various grammatical forms refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the present invention. Laboratory methods for preparing monoclonal antibodies are well known in the art (see, for example. Harlow et al., 1988). Monoclonal antibodies (mAbs) may be prepared by immunizing purified mutated FGFR3 into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al, and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Antibodies raised against mutated FGFR3 may be cross reactive with wild-type FGFR3. Accordingly a selection of antibodies specific for mutated FGFR3 is required. This may be achieved by depleting the pool of antibodies from those that are reactive with the wild-type FGFR3, for instance by submitting the raised antibodies to an affinity chromatography against wild-type FGFR3.

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C, and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Probe, primers, aptamers or antibodies of the invention may be labelled with a detectable molecule or substance, such as a fluorescent molecule, a radioactive molecule or any others labels known in the art. Labels are known in the art that generally provide (either directly or indirectly) a signal. The term "labelled", with regard to the probe, primers, aptamers or antibodies of the invention, is intended to encompass direct labelling of the probe, primers, aptamers or antibodies of the invention by coupling (i.e., physically linking) a detectable substance to the probe, primers, aptamers or antibodies of the invention, as well as indirect labeling of the probe, primers, aptamers or antibodies of the invention by reactivity with another reagent that is directly labeled. Other examples of detectable substances include but are not limited to radioactive agents or a fluorophore (e.g. fluorescein isothiocyanate (FITC) or phycoerythrin (PE) or Indocyanine (Cy5)). Examples of indirect labeling include detection of a primary antibody using a fluorescently labeled secondary antibody and end-labeling of a DNA probe with biotin such that it can be detected with fluorescently labeled streptavidin. An antibody or aptamer of the invention may be labelled with a radioactive molecule by any method known in the art. For example radioactive molecules include but are not limited radioactive atom for scintigraphic studies such as I123, I124, In111, Re186, Re188.

Preferably, step a) of the method of the invention further comprises the detection of a mutation in TERT gene, said detection being performed by:

- detecting a mutation selected from the group consisting of mutations 77C→T and 99C→T by reference to the nucleotide numbers of SEQ ID No 32.

Said mutations are disclosed in the publication Yves Allory et al. "Telomerase Reverse Transcriptase Promoter Mutations in Bladder Cancer: High Frequency Across Stages, Detection in Urine, and Lack of Association with Outcome", European association of urology.

The term "TERT" refers to the gene of telomerase reverse transcriptase. Its sequence is available under the accession number NC_000005.9.

In the context of the invention, for sake of clarity, the specific mutations are defined by reference to a specific fragment of TERT, as depicted in SEQ ID No 32. Said fragment corresponds to the complementary reverse sequence of position 1,295,301 to 1,295,152 of the sequence available under the accession number NC_000005.9.

Mutation 1,295,228C→T by reference to the TERT gene corresponds to the mutation 77C→T, by reference to SEQ ID No 32.

Mutation 1,295,250 C→T by reference to the TERT gene corresponds to the mutation 99C→T by reference to SEQ ID No 32.

These mutations are present in the promoter of the TERT gene. More precisely, mutations 1,295,228 C→T and 1,295,250 C→T, correspond to specific mutations on positions −124 and −146 from the translation start site in the promoter of TERT gene.

Typically, when detecting the TERT mutations, one case use the forward and reverse primers as follows:

```
                                        (SEQ ID No 33)
Forward TERT: 5' CCC TTC ACC TTC CAG CTC 3'

                                        (SEQ ID No 34)
Reverse TERT: 5' AGC GCT GCC TGA AAC TCG 3'
```

The probes useful are oligo in reverse. The appropriate sequences for detecting said specific mutations in the TERT gene are summarized in the table below:

TABLE 2

Sequences used for detecting the specific mutations on the TERT gene

| Mutation to detect | SEQ ID No | Core Sequence | Used Sequence |
|---|---|---|---|
| 77C→T | 35 | 5'CCCGGAAGGGGCT3' | 5' FAM/VIC-CCCGGAAGGGGCT-MGB 3' (SEQ ID No 35) tagged in 5' with FAM/VIC and coupled to a MGB to the 3' end. |
| 99C→T | 36 | 5'CCCGGAAGGGGTC-3' | 5' FAM/VIC-CCCGGAAGGGGTC-MGB 3' (SEQ ID No 36) tagged at 5' with FAM/VIC and coupled to a MGB to the 3' end. |

Measuring the Degree of Methylation of Gene of Interest

The method of the invention further comprises a step b) of measuring the degree of methylation of at least one gene selected from the group consisting of SEPTIN 9, SLIT 2, TWIST 1, HS3ST2 and fragments or variants thereof in a biological sample obtained from said subject in a second biological sample.

The inventors investigated the methylation of 18 genes and their role in the carciogenesis, especially in bladder cancer. They found out that methylation of SEPTIN 9, SLIT 2, TWIST 1, HS3ST2 are highly promising for diagnosing bladder cancer. The use of both assays of detecting specific mutations of FGFR3 and the determination of the methylation of SEPTIN 9, SLIT 2, TWIST 1, HS3ST2 genes provides unexpected results as for the specificity and sensibility of the diagnosis method.

"SEPTIN 9" or "SEPT9", or is part of a group of proteins called septins. Septins are involved in a process called cytokinesis, which is the step in cell division when the fluid inside the cell (cytoplasm) divides to form two separate cells. The septin-9 protein also seems to act as a tumor suppressor, which means that it regulates cell growth and keeps cells from dividing too fast or in an uncontrolled way. The sequence of the human SEPT9 gene is available online under the Ensemble accession number ENSG00000184640. In the context of the invention, the step b) of the method of the invention consist of detecting methylation of a fragment of SEPTIN9, as depicted in SEQ ID No 3. Alternatively, the step b) of the method of the invention consist of detecting methylation of a variant of SEPTIN9 having a percentage identity of at least 80%, preferably of at least 90%, more preferably of at least 98% with SEQ ID No 3.

"SLIT2" encodes for slit homolog 2. The sequence of the human SLIT2 gene is available online under the Ensemble accession number ENSG00000145147. In the context of the invention, the step b) of the method of the invention consist of detecting methylation of a fragment of SLIT2, as depicted in SEQ ID No 4. Alternatively, the step b) of the method of the invention consist of detecting methylation of a variant of SLIT2 having a percentage identity of at least 80%, preferably of at least 90%, more preferably of at least 98% with SEQ ID No 4.

"TWIST1" encodes for twist basic helix-loop-helix transcription factor 1. The sequence of the human TWIST1 gene is available online under the Ensemble accession number ENSG00000122691. In the context of the invention, the step b) of the method of the invention consist of detecting methylation of a fragment of TWIST1 as depicted in SEQ ID No 5. Alternatively, the step b) of the method of the invention consist of detecting methylation of a variant of TWIST1 having a percentage identity of at least 80%, preferably of at least 90%, more preferably of at least 98% with SEQ ID No 5.

"HS3ST2" encodes for heparan sulfate (glucosamine) 3-O-sulfotransferase 2. The sequence of the human HS3ST2 is available online under the Ensemble accession number ENSG00000122254. In the context of the invention, the step b) of the method of the invention consist of detecting methylation of a fragment of HS3ST2, as depicted in SEQ ID No 6. Alternatively, the step b) of the method of the invention consist of detecting methylation of a variant of HS3ST2 having a percentage identity of at least 80%, preferably of at least 90%, more preferably of at least 98% with SEQ ID No 6.

"DDR1" encodes for discoidin domain receptor tyrosine kinase 1. The sequence of the human DDR1 gene is available online under the Ensemble accession number ENSG00000204580. In the context of the invention, the step b) of the method of the invention consist of detecting methylation of a fragment of DDR1, as depicted in SEQ ID No 7. Alternatively, the step b) of the method of the invention consist of detecting methylation of a variants of DDR1 having a percentage identity of at least 80%, preferably of at least 90%, more preferably of at least 98% with SEQ ID No 7.

The determination of the degree of methylation of the genes of interest in a sample may be determined by different means. Non-limiting examples of methods suitable for measuring the degree of methylation according to the invention are:

- methylation-specific PCR;
- real-time methylation specific PCR;
- pyrosequencing;
- PCR Using Methylated DNA-specific binding protein, quantitative PCR, and DNA Chip Assay;
- detection of Differential Methylation—Methylation-Sensitive Restriction Endonuclease;
- detection of Differential Methylation—Bisulfate Sequencing Method;
- methylation-sensitive single-strand conformation analysis (MS-SSCA);
- high resolution melting analysis (HRM);
- methylation-sensitive single nucleotide primer extension (MS-SnuPE);
- base-specific cleavage; and
- microarray-based methods.

In one embodiment, step b) is performed by Methylation-specific PCR. When using the specific method of methylation-specific PCR on genomic DNA treated with bisulfite, cytosine in the 5'-CpG'-3 region remains intact, if it is methylated, but the cytosine changes to uracile, if it is unmethylated. Accordingly, based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

In one embodiment, step b) is performed by Real-time methylation specific PCR. Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using Sybergreen. Thus, the real-time methylation-specific PCR allows selective quantitative analysis of methylated DNA. Herein, a standard curve is plotted using an in vitro methylated DNA sample, and a gene containing no 5'-CpG-3' sequence in the base sequence is also amplified as a negative control group for standardization to quantitatively analyze the degree of methylation.

In one embodiment, step b) is performed by Pyrosequencing. The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

In one embodiment, step b) is performed by PCR Using Methylated DNA-specific binding protein, quantitative PCR and DNA Chip Assay. When a protein binding specifically only to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, McrBt.

In one embodiment, step b) is performed by Methylation-Sensitive Restriction Endonuclease. Detection of differential methylation can be accomplished by bringing a nucleic acid sample into contact with a methylation-sensitive restriction endonuclease that cleaves only unmethylated CpG sites. In a separate reaction, the sample is further brought into contact with an isoschizomer of the methylation-sensitive restriction enzyme that cleaves both methylated and unmethylated CpG-sites, thereby cleaving the methylated nucleic acid.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed. As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination. Examples of other methylation-sensitive restriction enzymes include, but are not limited to SacII and EagI.

The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

In one embodiment, step b) is performed by Bisulfate Sequencing Method. In this method, the detection of a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfite sequencing for detection of methylated nucleic acid.

Enhanced Method of Diagnostic

Preferably, step a) and step b) are performed on the same biological sample. More preferably, said steps a) and b) are performed on the same nucleic material, preferably the same DNA. Even more preferably, said DNA is a bisulfite treated DNA. Consequently, in a more preferred embodiment, said step a) and step b) are performed on the same DNA of the patient, which was previously treated with bisulfite. Typically step a) and step b) are performed simultaneously.

In this specific embodiment, step a) is a step of determining the presence of:

- a guanine (G) in position 746 of the sequence depicted in SEQ ID No 1 which was bisulfite treated;
- a thymine (T) in position 1114 of the sequence depicted in SEQ ID No 1 which was bisulfite treated; and/or
- a guanine (G) in position 1124 of the sequence depicted in SEQ ID No 1 which was bisulfite treated.

Said mutations respectively correspond to mutations Ser249Cys, Gly372Cys and Tyr375Cys by reference to the amino acid numbers of SEQ ID No 2.

Thus, in one preferred embodiment, step a) is a step of detecting a mutation in the FGFR3 gene on a bisulfite treated DNA version of the sequence as depicted in SEQ ID No 1.

As used herein, the expression "bisulfite treated DNA version of the sequence as depicted in SEQ ID No 1" refers to the sequence of the FGFR3 gene which was treated with bisulfite. Treatment of DNA with bisulphite converts cytosine residues to uracil, but leaves 5-methylcytosine residues unaffected. Thus, bisulphite treatment introduces specific changes in the DNA sequence that depend on the methylation status of individual cytosine residues, yielding single-nucleotide resolution information about the methylation status of a segment of DNA.

Consequently, a bisulfite treated DNA version of the sequence depicted in SEQ ID No 1 is a sequence in which all the cytosine are replaced by uracile, except for the methylated cytosine of a CpG dinucleotide.

In this specific embodiment, step a) consists of determining the presence of a guanine (G) in position 746;
the presence of a thymine (T) in position 1114; and/or
the presence of a guanine (G) in position 1124;
of the sequence depicted in SEQ ID No 1 after it was bisulfite treated.

In a most preferred embodiment, step a) and step b) are performed in the same bisulfited treated DNA obtained from a single biological sample. The invention thus provide for an efficient, quick and cost effective method for the surveillance, diagnosis and screening of a bladder cancer, or a risk of a developing a bladder cancer in a subject.

In this specific embodiment, step a) is a step of detecting a mutation in the FRGF3 gene as follows:

| Mutation to detect (by reference to SEQ ID No 2) | Mutation to detect by reference to SEQ ID No 1 without any bisulfite treatment | Mutation to detect by reference to SEQ ID No 1 after a bisulfite treatment |
|---|---|---|
| Ser249Cys | T**C**C ⇒ T**G**C | T**T**T ⇒ T**G**T |
| Gly372Cys | **G**GC ⇒ **T**GC | **G**GT ⇒ **T**GT |
| Tyr 375Cys | T**A**T ⇒ T**G**T | T**A**T ⇒ T**G**T |

In a preferred embodiment, the method of the invention comprises a further step b') after step b) of comparing the degree of methylation measured in step b) to a threshold value, wherein said threshold value distinguishes between patient suffering or at risk of developing a bladder cancer and patient who do not suffer from bladder cancer.

In some embodiments, the methylation degree of at least one cytosine is compared to the methylation degree of a control locus. In some embodiments, the control locus is an endogenous control. In some embodiments, the control locus is an exogenous control. Typically, said control locus is found in a housekeeping gene.

As used herein, a "threshold value that distinguishes between patient suffering or at risk of developing a bladder cancer and patient who do not suffer from bladder cancer" refers to a value or range of values of a particular measurement that can be used to distinguish between samples from individuals with the bladder cancer and samples without said cancer. Ideally, there is a threshold value or values that absolutely distinguishes between the two groups (i.e., values from the diseased group are always on one side (e.g., higher) of the threshold value and values from the healthy, non-diseased group are on the other side (e.g., lower) of the threshold value). Typically, said threshold value is obtained empirically.

Preferably, step b) is performed of methylation-specific PCR (MSP) in multiplex mode (MSPM). MSPM has the major advantage of a decrease in the number of PCRs required relative to the monoplex mode. Thus, the multiplex mode offers a time saving, as it is quicker than several monoplexes, and is economically advantageous.

"Multiplex PCR" means a form of PCR, generally quantitative PCR, permitting simultaneous amplification of several targets of interest in a single step, using one or more specific primers. This technique is very advantageous for determining the presence of deletions, mutations, polymorphisms or hypermethylations of several markers.

In contrast, the expression "Monoplex PCR" refers to a form of PCR, generally a quantitative PCR, permitting amplification of a single target of interest.

"Methylation-specific PCR" or "MSP" refers to a technique for measuring the degree of methylation of a gene. This technique is based on the principle of quantitative PCR. Typically, this technique is based on treating the DNA sample to be investigated with sodium bisulfite. This treatment makes it possible to transform each of the unmethylated cytosines into uracils in the treated DNA. The sample thus treated then undergoes a PCR with primers specific to the genes to be treated. Determination of the nature of the specific primers depends on the nucleotide sequence to be amplified. In the context of this invention, methylation-specific PCR is preferably employed in multiplex mode, and is then called Methylation-Specific PCR in multiplex mode, or MSPM.

For determining the degree of methylation of the targeted genes by the MSP, the inventors modified DNAs by the EZ DNA Methylation Kit (Zymo Research) or with the Epitect bisulfite kit (Qiagen) so that they are compatible to the achievements of the QM-MSP.

More specifically, they used the TaqMan technology for the QM-MSP. Said method is adapted for the purpose of the invention since it can accurately determine the percentage of methylated copies of each gene target in a single PCR.

Typically, TaqMan-MGB probes comprise:

- a fluorophore at the 5'end such as 6FAM, VIC, TET, NED, and
- a quencher coupled to the non-fluorescent molecule MGB (Minor Groove Binder) to the 3' end.

MGB allows the molecule by inserting itself into the double helix of DNA to increase the specificity of hybridization. Typically, the primers and TaqMan-MGB probes are generated by taking into account the modification of the DNA by treatment with sodium bisulfite. The Primers and probes of target genes containing of CpG sites have thus to be designed to amplify only the methylated alleles.

Typically, the housekeeping gene (Albumin, β-Actin, β-Globin) are used to normalize the DNA amounts by using a primer/probe set not containing CpG sites.

Typically, target sequences for amplification have a size of about 100 bases.

The degree of methylation is calculated by the quantification techniques that are well known by a person skilled in the art. This quantification can be absolute or relative. Preferably, it is calculated by the so-called ΔΔCt technique. This method employs an arithmetic formula for expressing the degree of methylation of a target gene, by normalizing with a reference gene. First, the differences ΔCt between the values of Ct of the target gene and of the reference gene are determined for the sample to be analyzed and the standard DNA. The standard DNA is typically a universally methylated DNA. It allows normalization of the degrees of methylation of the genes. A DNA of this kind is for example marketed by the company Zymo Research under the trade reference D5011. Following modification using a suitable kit, such as the commercial kit EZ DNA Methylation (ref. D5002, Zymo Research), this standard DNA is used as reference.

$$\Delta Ct_{sample}=Ct(\text{target}_{sample})-Ct(\text{reference}_{sample})$$

$$\Delta Ct_{standard}=Ct(\text{target}_{standard})-Ct(\text{reference}_{standard})$$

Then ΔΔCt between the standard and the sample is calculated:

$$\Delta\Delta Ct=\Delta Ct_{standard}-\Delta Ct_{sample}$$

The method of calculation of the ΔΔCt values assumes that the efficiencies of PCR amplification of the 2 genes are equal to 100%. Thus, in other words, this method of calculation assumes that the concentration of products is doubled at each cycle of the exponential phase of PCR. It is therefore deduced from this that the normalized degree of methylation of a target gene is determined by the formula:

$$2^{-\Delta\Delta Ct}=2^{(Ctgene\text{-}Ct\ referenc)\ standard\text{-}(Ctgene\text{-}Ctreferncе)_{sample}}$$

This method gives a relative degree of methylation as a function of the positive control used (standard DNA). Moreover, it takes into account the variations in the copy number of the reference gene used. These variations are necessarily due to the variations in the amount of DNA that was used for carrying out the PCR. Thus, the results are not distorted by the nature of the reference gene. Preferably, the reference gene is a housekeeping gene. More preferably, it is the albumin gene or a fragment thereof.

Preferably, step b) of the method of the invention comprises simultaneous measurement of the degrees of methylation:

- of the SEPTIN9, SLIT2 and albumin genes, or fragments thereof,
- of the SEPTIN, SLIT 2 genes or fragments thereof,
- of the SEPTIN9 and albumin gene or fragments thereof,
- of the SLIT2 and albumin genes or fragments thereof,
- of the TWIST 1, HS3ST2 and albumin genes or fragments thereof,
- of the TWIST1 and HS3ST2 genes or fragments thereof,
- of the TWIST 1 and albumin genes or fragments thereof,
- of the HS3ST2 and Albumin genes or fragments thereof.

More preferably, step b) of the method of the invention comprises simultaneous measurement of the degrees of methylation of all of the SEPTIN9, SLIT2, TWIST 1 and HS3ST2 genes or fragments thereof. More preferably, said fragments are SEQ ID No 3, 4, 5 and 6.

Typically, for determining the degree of methylation, one can use the forward and reverse primers and probes as defined bellows. The methylation sites are underlined and in bold.

TABLE 2

Primers and probe for measuring the degree of methylation of the target genes of the invention

| Detection of methylation | Name | SEQ ID No | | Number of CgG sites targeted |
|---|---|---|---|---|
| SEPTIN9 | Forward | 16 | 5' TTT TTT CGT CGT TGT TTT TCG C 3' | 4 |
| | Reverse | 17 | 5' ATC CGA AAT AAT CCC ATC CAA CTA C 3' | 1 |
| | Probe | 18 | 5' FL- ATT ATG TCG GAT TTC GC 3'-MGB | 3 |
| SLIT2 | Forward | 19 | 5' TAG TTT CGT CGG GTA TTG GGT TT 3' | 2 |
| | Reverse | 20 | 5' TCG CCG ACA CTA AAA ACT TTC TTT AA 3' | 2 |
| | Probe | 21 | 5' FL- AGA TAT TGC GCG GTT TT 3'-MGB | 2 |
| TWIST1 | Forward | 22 | 5' GAC GGT GTG GAT GGT TTC GA 3' | 2 |
| | Reverse | 23 | 5' ACT CTA CAA CAC CGA CAC CGT TTC 3' | 2 |
| | Probe | 24 | 5' FL- AGC GTT TAA CGG TTG GAC 3'-MGB | 3 |
| H83812 | Forward | 25 | 5' GCG CGG GGT TAT TTT AGT CG 3' | 3 |
| | Reverse | 26 | 5' CAA ATC GTC GCA ACA ACA CAA A 3' | 2 |
| | Probe | 27 | 5' FL- CGT AAA AAC GAA AAA CAA C 3'-MGB | 2 |
| DDR1 | Forward | 28 | 5' AGG TTT GTT TTG AGG ATT TTT GAG TTT 3' | 0 |
| | Reverse | 29 | 5' CCT TCT CCT CTC AAT TCC TCT CTC TAA 3' | 0 |
| | Probe | 30 | 5' CGT TTG GAT TTT CGG GTT T 3'-MGB | 2 |

The method of the invention shows unexpected results with regards to the sensibility and the specificity of the method of diagnosing bladder cancer.

As used herein, the expression "True Positive" or "TP" refers to a patient who suffers from the targeted has the disease and whose test is positive.

As used herein, the expression "False Positive" or "FP" refers to a patient who does not suffer from the targeted disease but whose test is positive.

As used herein, the expression "True Negative" or "TN" refers to a patient who does suffer from the targeted disease and whose test is negative.

As used herein, the expression "False Negative" or "FN" refers to a patient who does suffer from the targeted disease but whose test is negative.

When evaluating the efficiency of a diagnosing method for a targeted disease, the sensitivity and specificity of the test is determined.

The sensitivity and specificity of a quantitative test are dependent on the cut-off value above or below which the test is positive.

As used herein, the term "sensitivity" refers to the ability of a diagnosing method to correctly identify the patients suffering from the targeted disease.

The sensitivity of a diagnosing method is determined as follows:

$$\text{Sensitivity}=TP/(TP+FN)$$

As used herein, the term "specificity" refers to the ability of a diagnosing method to correctly identify the patients who do not suffer from the targeted disease.

The specificity of a diagnosing method is determined as follows:

$$\text{Specificity}=TN/(TN+FP)$$

In some embodiments, threshold values provide a specified sensitivity and specificity for detection of a bladder cancer. Typically, the threshold value allows for at least a 50%, 60%, 70%, or 80% sensitivity and specificity for detection of a bladder cancer in a subject.

The inventors have shown that the combination of two assays aiming to:

- on one hand, identify specific mutation of FGFR3, and
- on the other end, measure the degree of methylation of specific genes of interest provide an accurate method for diagnosing bladder cancer, showing a high specificity, as well as a high sensibility.

The selection of a specific sensibility and a specific is dependent on the chosen threshold value.

Typically, threshold values are expressed in cumulative methylation index (CMI), which consists in the sum of the one, two, three, and four methylation values for each tested sample.

Typically, said threshold is obtained by adding up the methylation values of the four mentioned genes (cumulative methylation index or CMI) and is used in an algorithm that calls the patient as positive if the mutation is present or if the mutation is not present and the CMI value is higher than a given threshold, so obtaining the desired combination of values of Sensitivity/Specificity/CMI threshold. Said combinations are disclosed in table 5.

Typically, the threshold value is comprised between 1 and 54 CMI, preferably said threshold is selected in the table 5 below:

TABLE 5

Combination of Sensitivity/Specificity/CMI threshold

| Threshold (CMI) | Sensitivity | Specificity | Application |
|---|---|---|---|
| 1.39 | 91 | 70 | Screening |
| 1.61 | 89 | 75 | |
| 2.38 | 85 | 80 | |
| 3.53 | 85 | 85 | |
| 5.05 | 83 | 90 | |
| 10.17 | 83 | 95 | |

TABLE 5-continued

| Combination of Sensitivity/Specificity/CMI threshold | | | |
|---|---|---|---|
| Threshold (CMI) | Sensitivity | Specificity | Application |
| 12.52 | 83 | 98 | |
| 22.27 | 78 | 100 | |
| 53.99 | 70 | 100 | Surveillance & |
| 16.12 | 80 | 99 | Diagnosis |
| 3.53 | 85 | 85 | |
| 1.59 | 90 | 74 | |
| 0.98 | 95 | 64 | |
| 0.96 | 98 | 64 | |
| 0.44 | 98 | 50 | |

The table above gives valuable information on specificity and sensitivity of the test of the invention, depending on the chosen threshold.

The one skilled in the art would know how to choose the threshold value, depending on the targeted application such as screening or surveillance and diagnosis.

Measuring the Level of Expression of a Gene

In one embodiment, the method of the invention further comprises a step c) of measuring the level of expression of a gene selected from the group consisting of BCLA-4, BCAR-1. Preferably, the method further comprises a step c') of comparing the level of expression to the level of expression obtained in a healthy subject or a subject who overcame bladder cancer.

BLCA-4 is disclosed in the publication Van Le et al., Functional Characterization of the Bladder Cancer Marker, BLCA-4, Clinical Cancer Research, vol. 10, 1384-1391, Feb. 15, 2004.

BCAR-1 refers to the gene of breast cancer anti-estrogen resistance protein 1. Several isoforms of said protein are available. As used herein, BCAR-1 refers to any one of the following protein:

Isoform 1: available under the accession number NP_001164185.1;

Isoform 2: available under the accession number NP_001164186.1;

Isoform 3: available under the accession number NP_001164187.1;

Isoform 4: available under the accession number NP_001164188.1;

Isoform 5: available under the accession number NP_001164189.1;

Isoform 6: available under the accession number NP_055382.2;

Isoform 7: available under the accession number NP_001164190.1;

Isoform 8: available under the accession number NP_001164191.1; and

Isoform 9: available under the accession number NP_001164192.1.

In one embodiment, step c) of measuring the level of expression of said gene(s) is a step of measuring the expression level of translation products of said gene(s), preferably proteins.

Methods for measuring the quantity of protein in a biological sample may be measured by using standard immunodiagnostic techniques, including immunoassays such as competition, direct reaction, or sandwich type assays. In such embodiments, cancer cells are purified from the isolated biological sample. Such assays include, but are not limited to, agglutination tests; enzyme-labelled and mediated immunoassays, such as ELISAs; biotin/avidin type assays; radioimmunoassays; immunoelectrophoresis; immunoprecipitation.

The reactions generally include revealing labels such as fluorescent, chemiluminescent, radioactive, enzymatic labels or dye molecules, or other methods for detecting the formation of a complex between the antigen and the antibody or antibodies reacted therewith.

More preferably, an ELISA method can be used, wherein the wells of a microtiter plate are coated with a set of antibodies against the target protein of the invention. The cancer cells of the biological sample that are suspected of containing a target protein, are then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

A Human BLCA-4 Elisa kit is available and is marketed by the company CUSABIO. Therefore, the step c) of measuring the level of expression of BLAC-4 can be performed by ELISA, more preferably by the kit CUSABIO. Preferably, step c) of measuring the level of expression of said gene(s) is a step of measuring the expression level of translation products by ELISA of a gene selected from the group consisting of BCLA-4, BCAR-1.

In a particular embodiment, the methods of the invention comprise contacting the cancer cells of the biological sample with a binding partner capable of selectively interacting with at least one of proteins encoded by one of the genes selected among of BCLA-4, BCAR-1 present in the biological sample. The binding partner may be an antibody that may be polyclonal or monoclonal, preferably monoclonal. In another embodiment, the binding partner may be an aptamer.

In a preferred embodiment, the method of the invention further comprises a step c'), further to step c) of comparing the expression profile obtained in step c) with cut-off value(s).

Alternatively, the method of the invention further comprises a step c''), further to step c) of comparing the expression profile obtained in step c) with the expression profile of said gene(s) obtained for at least one control selected from the group consisting of a positive control and a negative control.

This step of comparing the expression profile obtained in step c) to a cut-off value or to the expression profiles of a control is useful to identify subjects presenting bladder cancer.

As used herein, the term "expression profile" refers to quantitative and qualitative expression of one or more genes in a sample. The expression profile of a single gene corresponds to the expression level of said gene. The expression profile is a repository of the expression level data that can be used to compare the expression levels of different genes, in whatever units are chosen. The term "profile" is also intended to encompass manipulations of the expression level data derived from a cell, tissue or individual. For example, once relative expression levels are determined for a given set of genes, the relative expression levels for that cell, tissue or individual can be compared to a standard to determine if expression levels are higher or lower relative to the same genes in a standard. Standards can include any data deemed by one of skilled in the art to be relevant for comparison, for example determined threshold value or expression profile of a positive and/or negative control.

As used herein, the expression "comparing the expression profile" in all its grammatical forms, refers to the evaluation of the quantitative and/or qualitative difference in expression of a gene. Typically, the person skilled in the art may compare the level of expression of a gene to a cut-off value.

Typically, a "cut-off value" can be determined experimentally, empirically, or theoretically. A threshold value can also be arbitrarily selected based upon the existing experimental and/or clinical conditions, as would be recognized by person skilled in the art. Preferably, the person skilled in the art may compare the expression profile of given gene according to the invention with cut-off value for said gene. For each gene to be compared to a cut-off value, the skilled person in the art will compare the level of expression of said gene to a cut-off value.

In another embodiment, the step c") is a step of comparing the expression profile obtained in step c) with the expression profile of at least one control chosen in the group consisting of a positive control and a negative control.

In this particular embodiment, said positive control is the expression profile of a subject suffering from bladder cancer or a subject who died from bladder cancer.

Preferably, said negative control is the expression profile of a healthy subject or a subject who overcame bladder cancer.

The expression profile of the gene(s) of interest of the present invention is set for said positive and negative controls. The person skilled in the art is thus able to compare the expression profile of the gene(s) of interest in the biological sample of said subject to the expression profile of a positive and/or a negative control. Such comparison will then lead the person skilled in the art to determine the prognosis of a subject.

Therapeutic Method According to the Invention

The invention relates to a method of treatment of a patient suffering from bladder cancer comprising the steps of:

1) predicting the prognosis of a subject by
   a) detecting a mutation in the FGFR3 gene in a first biological sample by detecting a mutation selected from the group consisting of mutations NM_001163213.1 by reference to the nucleotide numbers of SEQ ID No 1; or by detecting a mutation in the group consisting of mutations Arg248Cys, Ser249Cys. Gly372Cys, and Tyr375Cys, by reference to the amino acid numbers of SEQ ID No 2; and
   b) measuring the degree of methylation of at least one gene selected from the group consisting of SEPTIN 9, SLIT 2, TWIST 1, HS3ST2 and fragments or variants thereof in a second biological sample obtained from said subject; and then
2) if said step 1)a) shows the presence of a mutation and if step 1)b) shows a methylation of one of said genes, then the method of the invention comprises a step 3) of providing the appropriate therapy to said patient.

All the technical features disclosed above are applicable.

In the context of the invention, the term "treating" or "treatment", as used herein, means reversing, alleviating, inhibiting the progress of, or preventing the disorder or condition to which such term applies, or reversing, alleviating, inhibiting the progress of, or preventing one or more symptoms of the disorder or condition to which such term applies.

Kit According to the Invention

The invention also relates to a kit comprising:

(i) at least one primer suitable for detecting a mutation in the FGFR3 gene selected among mutations Arg248Cys, Ser249Cys, Gly372Cys, and Tyr375Cys, by reference to the amino acid numbers of SEQ ID No 2; and
(ii) at least one primer and at least one probe for measuring the degree of methylation of a gene selected from the group consisting of SEPTIN 9, SLIT 2, TWIST 1, HS3ST2 and fragment or variant thereof.

The invention also relates to a kit comprising:

(a) at least one oligonucleotide selected from the group consisting of SEQ ID No 8 to 13; and
(b) at least one oligonucleotide selected from the group consisting of SEQ ID No 16 to 30.

In a further embodiment, the kit of the invention further comprises:

(c) at least one oligonucleotide selected from the group consisting SEQ ID No 33 to 36.

Said kit is for diagnosing bladder cancer.

All the technical features disclosed above are applicable.

FIGURE LEGENDS

FIG. 1: Illustration of the implementation of Quantitative Real-Time Multiplex-Methylation Specific Polymerase Chain Reaction (QM-MSP).

Figure 2:
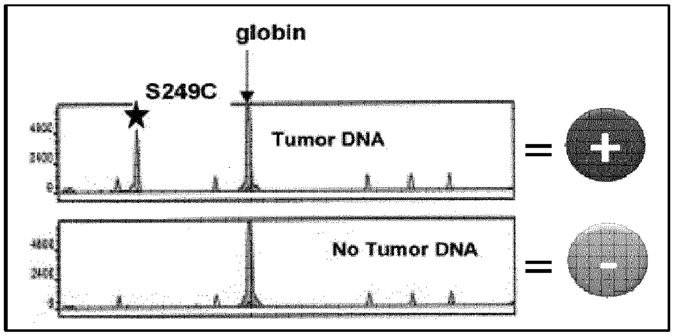

FIG. 2: Detection of the S249C mutation detection in patients with cancer of the bladder (+) versus an individual without the mutation S249C (−).

Figure 3:
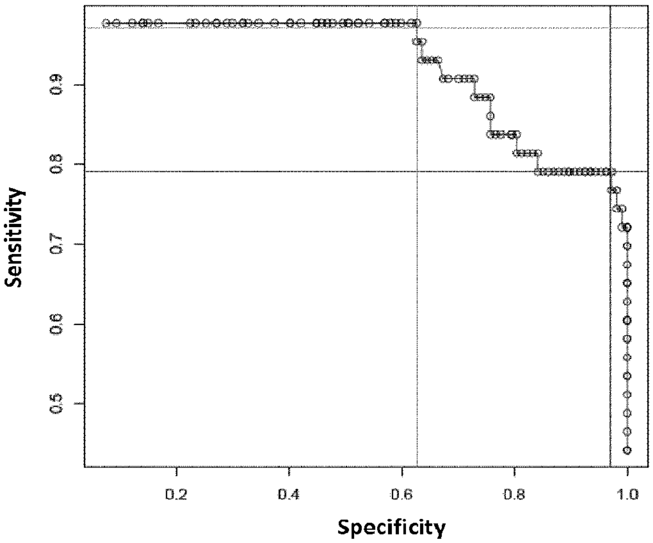

FIG. 3: Determination of the Specificity and the sensibility of the method of the invention using ROC curves.

Figure 4:
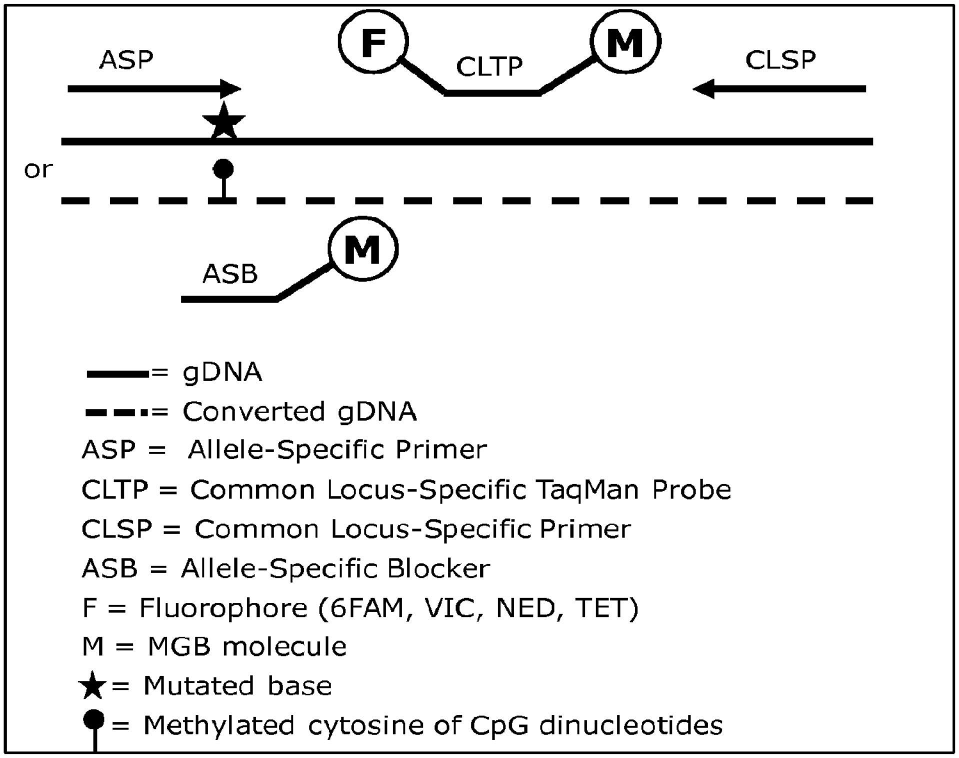

FIG. 4: Illustration of the implementation of the competitive Allele-Specific TaqMan PCR (Cast-PCR).

Figure 5:
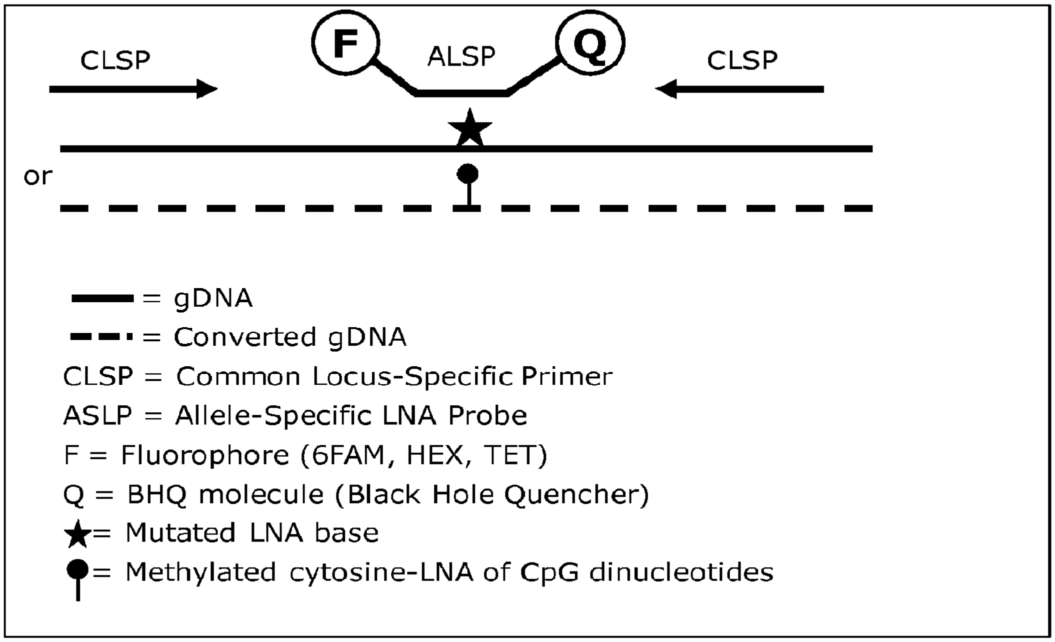
Figure 6:
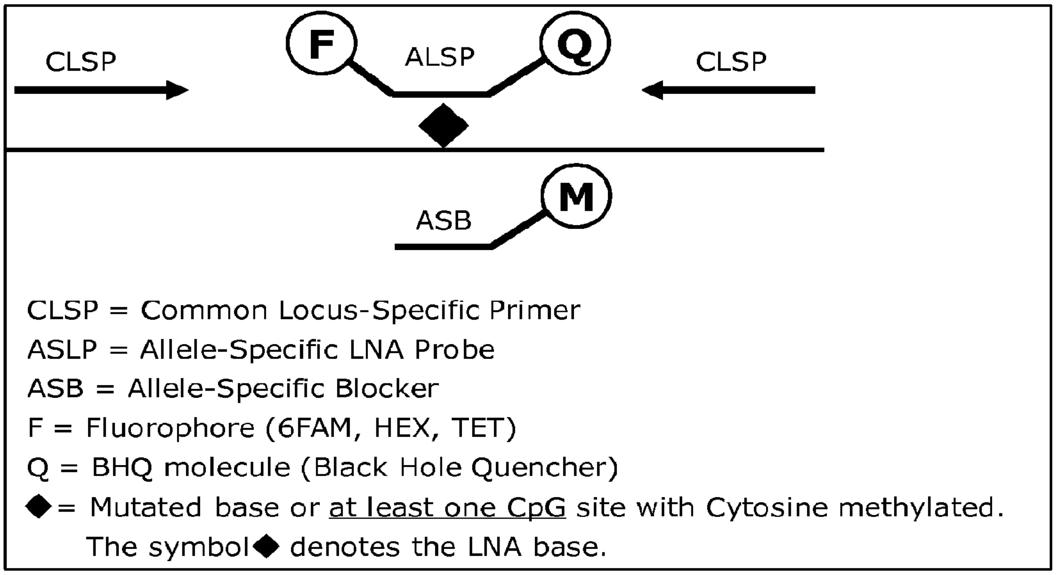
Figure 7:
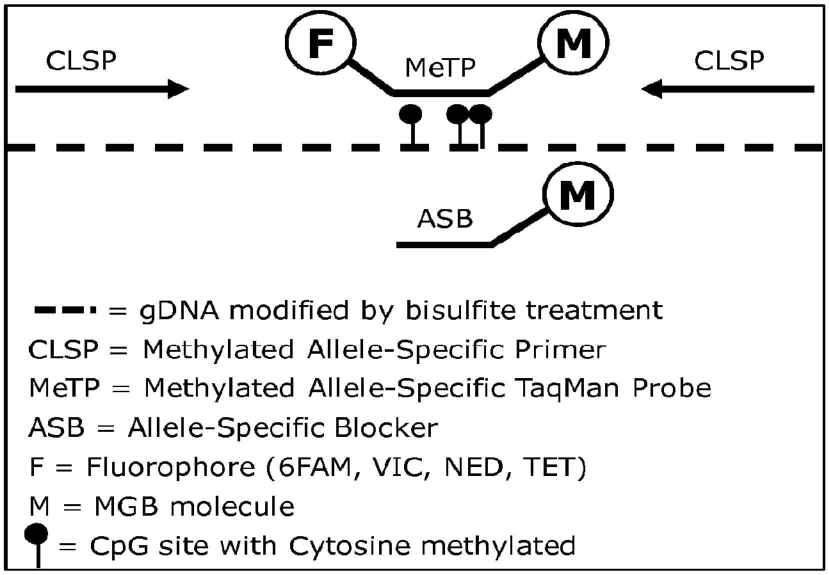

FIG. 5: Illustration of the implementation of Locked Nucleic Acid technology (LNA) Probe FIG. 6: Illustration of the implementation combining the Locked Nucleic Acid technology (LNA) Probe with a MGB oligonucleotide blocker that suppresses the wild type allele FIG. 7: Illustration of the implementation combining QM-MSP with a MGB oligonucleotide blocker that suppresses the unmethylated allele

EXAMPLES

Example 1: Evaluation of Sensitivity and Sensibility of Diagnosing Method and Kits of Prior Art Currently, several FDA-approved test of diagnosing bladder cancer are marketed. Said approved tests include:

- the bladder tumor antigen BTA TRIAK test (Polymedco, Cortlandt Manor, N.Y., USA),
- the nuclear matrix protein (NMP) 22, and NMP22 BladderChek assays (Matritech, Newton, Mass., USA),
- ImmunoCyt test (Diagnocure Inc, Quebec City, Quebec, Canada), and
- fluorescence in situ hybridization (FISH) analysis (Urovysion Systems Vysis, Abbott Laboratories, Abbott Park, Ill., USA) [16].

The BTA-TRAK is a standard ELISA that quantitatively measures the amounts of a complement factor H-related protein and complement factor H in urine. It is used as aid in the management of bladder cancer in combination with cystoscopy.

The NMP-22 test is a quantitative microtiter sandwich ELISA that uses two antibodies, each of which recognizes a different epitope of the nuclear mitotic apparatus. The FDA has approved this test for use as an aid in the diagnosis of patients at risk for or with symptoms of bladder cancer.

CYFRA 21-1 is a soluble fragment of cytokeratin 19 that is measured either by a solid phase sandwich immunoradiometric assay (Cis-Bio) or an electrochemiluminescent immunoassay (Roche Diagnostic).

Telomeres are repetitious sequences that cap the end of the chromosomes. They protect chromosomal ends and thereby maintain genomic stability. Telomerase activity is measured by TRAP, which involves PCR amplification of in vitro telomerase reaction products. Telomerase was not grade sensitive, but false-positive results were obtained in cases of chronic or severe bladder inflammation because of the presence of lymphocytes.

ImmunoCyt. Immunocytology is based on the visualization of tumor-associated antigens in urothelial carcinoma cells using monoclonal antibodies. ImmunoCyt is a commercially available immunocytologic assay that uses fluorescein-labeled monoclonal antibodies M344 and LDQ10 directed against sulfated mucin glycoprotein and a Texas red-linked monoclonal antibody 19A211 against glycosylated forms of high molecular carcinoembryonic antigens to detect bladder cancer cells. The time-consuming microscopic examination of the slides remains a disadvantage and the reproducibility is cytologist dependence.

UroVysion test or Multitarget Multicolor FISH Assay. Cytogenetic studies reveal frequent alterations in many chromosomes. Chromosomal abnormalities can be detected by FISH. The UroVysion test is a multitarget multicolor FISH assay that involves staining of exfoliated cells from urine specimens with the centromeric fluorescent denatured Chromosome Enumeration Probe for chromosome 3, 7, 17, and the locus Specific Identifier probe for 9p21, and observing the cells under a fluorescence microscope. Based on case-control and cohort studies, the UroVysion test appears to be a promising test for detecting bladder cancer. It may have an ability to detect bladder tumor recurrence before its clinical detection. However, the test also a low sensitivity to detect low-grade bladder tumors.

Predictive Biosciences by The CertNDx™ Bladder Cancer Assay offers a monitoring solution that analyzes a urine sample for bladder cancer recurrence. The test utilizes a combination of DNA and protein biomarkers.

Taken together, these tests lack of accuracy (low ratio sensitivity/specificity) of a marker in diagnosis bladder cancer to avoid too many false-positive and false-negative, as shown in table 6. This results thus confirm that there is a unfulfilled need for additional accurate biomarkers. Thus, the development of noninvasive and accurate diagnostic biomarkers of bladder tumor detection is imperative and crucial to improve the prognosis, diagnosis and the screening of bladder tumor.

TABLE 6

Bladder tumor markers beyond cytology.

| Test/Marker | Technical | Company | Sensitivity (%) | Specificity (%) |
|---|---|---|---|---|
| | | OncoDiag ® | | |
| Urotest | Multiplex qPCR | Diagnosis/Surveillance | 98 | 67 |
| | | Screening | 80 | 97 |
| Hematuria* | Dipstick | Standard | 1-5 | 95 |
| Cytotogy* | Microscopy | Standard | 20 | 90 |
| BTA-TRAK* | Elisa | Polymedco Inc, US | 57 | 50 |
| NMP-22* | Elisa | Matritech Inc, US | 47 | 55-80 |
| CYFRA 21-1* | Elisa | Cis-Bio, Roche, France | 75 | 67-71 |
| TRAP assay* | PCR | Qbiogene, US | 70 | 60-70 |
| ImmunoCyt* | Microscopy | DiagnoCure Inc, Canada | 38 | 73-80 |
| UroVysion* | FISH | Vysis/Abbott, US | 68 | 90 |
| Predictive Biosciences | Elisa + qPCR | CertNDX for recurrence monitoring, US | 3 possible results (negative positive, intermediate) | |

Source: International consensus panel on bladder tumor markers. *Journal Urology*, 2005.

Example 2: Development of an Urine Based Test of a Molecular Approach Combining Both Genetic and Epigenetic Assays Study Design During the pre-validation phase, a total number of 153 urines including 107 controls and 48 patients with initial superficial bladder tumors (histological stage pTa and pT1) were selected. A cystoscopic examination coincided with urine collection for molecular analysis. A transurethral resection has been performed for each patient with bladder cancer. All patients were informed and gave their written consent.

Urine Collection and DNA Extraction

Freshly voided urine (100 ml) was collected before cystoscopy and stored at 4° C. until DNA preparation. Cells were pelleted by centrifugation for 10 minutes at 1,500×g. Cell pellets were washed twice with 10 mL PBS, resuspended in 1 mL PBS, transferred to a microtube (Eppendorf), and collected by centrifugation for 10 minutes at 1,500×g. Supernatant was discarded and the cell pellet was stored at −20° C. until DNA isolation. DNA was extracted using the QiAamp DNA Blood Mini kit (Qiagen) or ZR DNA Urine kit (Zymo Research) according to the manufacturer's protocol. The DNA concentration was measured fluorometrically with Picogreen quantification reagents (Bioprobes; Interchim).

FGFR3 Mutation Analysis

Ten different FGFR3 mutations have been described in bladder cancer, but 4 of them (S249C, Y373C, G370C, and R248C) account for 95% of cases.

These mutations therefore represent an excellent target for assays, such as allele specific PCR (AS-PCR), that depend on the specific detection of point mutations.

PCRs were carried out in a thermocycler (Eppendorf, Life technologies).

Preferably, PCR was performed in a final volume of 10 μL containing 5 ng of genomic DNA, IX PCR buffer (Perkin-Elmer Taq polymerase buffer), 200 μM each of the deoxynucleoside triphosphate, 2 mM MgCl2, 0.9 μL of dimethyl sulfoxide, 2.5 U of gold Taq polymerase (Perkin-Elmer), and primers (Forward and Reverse) at the concentrations of 200 nM each.

In each multiplex PCR, each pair includes:

one forward primer tagged in 5' with a specific fluorescent dye (6FAM, HEX, and TET) and one reverse primer presenting a nucleotide modified in 3' by Locked Nucleic Acid technology (LNA).

In both PCRs (PCR1, PCR2) the β-globin gene was included as an internal control. For each primer pair, a fluorescent primer was used to label the PCR product. All primers were obtained from Applied Biosystems. PCR products were analyzed on an ABI PRISM 310 capillary DNA sequencer with the Genscan software.

PCR1 detects the R248C. G372C mutations, and P3-globin. The primers used are as follows:

Forward F1/Reverse R2 for detecting mutation R248C,

Forward F2/Reverse R3 for detecting mutation G372C, and Forward FGLO/Reverse RGLO for detecting β-globin PCR2 detects the R249C, Y375C mutations, and β-globin. The primers used are as follows:

Forward F1/Reverse R1 for detecting R249C,

Forward F2/Reverse R4 for detecting Y375C, and Forward FGLO/Reverse RGLO for detecting β-globin.

Cycling conditions were as follows:

| Stage | Temp | Time | Cycles |
|---|---|---|---|
| 1 | 96° C. | 6 min | 1 |
| 2 | 95° C. | 15 sec | 40 |
| | 61° C. | 15 sec | |
| | 72° C. | 15 sec | |
| 3 | 72° C. | 1 min | 1 |

Quantitative Real-Time Multiplex-Methylation Specific Polymerase Chain Reaction (QM-MSP)

The inventors evaluated promoter methylation for 18 genes that are important in the carcinogenesis and potentially in the bladder cancer, as COL1A2, DDR1, DIRAS3, DNASEIL1, EYA4, FASTK, HS3ST2, NPY, NTRK3, PENK, SEMA3B, SEPTIN5, SEPTIN9, SLIT2, SYNE1, TGFB, TWIST 1 and WIF1 genes.

DNAs have been modified by the EZ DNA Methylation Kit (Zymo Research) or with the Epitect bisulfite kit (Qiagen) so that they are compatible to the achievements of the QM-MSP.

The inventors used the TaqMan technology for the QM-MSP. It can accurately determine the percentage of methylated copies of each gene target in a single PCR.

TaqMan-MGB probes comprise:

a fluorophore, 6FAM, VIC, TET, NED for example, the 5'end and a quencher coupled to the non-fluorescent molecule MGB (Minor Groove Binder) to the 3' end.

MGB allows the molecule by inserting itself into the double helix of DNA to increase the specificity of hybridization.

The primers and TaqMan-MGB probes were generated by taking into account the modification of the DNA by treatment with sodium bisulfite. The primers and probes of target genes containing of CpG sites have been designed to amplify only the methylated alleles. The schematic of QM-MSP is noted in FIG. 1. The housekeeping gene (Albumin, β-Actin, β-Globin) was considered to normalize the DNA amounts by using a primer/probe set not containing CpG sites.

Target sequences for amplification have a size of about 100 bases. The primers final concentration should be 100 nM and 900 nM. Probe concentration should be between 100 nM and 300 nM. Preferably, the solution of modified DNA is added to a final concentration of 400 nmol of each primer (forward and reverse) and the final concentration of 250 nmol of TaqMan probe-MGB and IX PCR solution (Quantitect Multiplex-Qiagen or Kapa-Biosystems). The reaction volume is 20 μL.

Thermal-Cycling Profile:

Using the Quantitect Multiplex (Qiagen):

| Stage | Temp | Time | Cycles | Data collection |
|---|---|---|---|---|
| 1 | 50° C. | 2 min | 1 | No |
| 2 | 95° C. | 15 min | 1 | No |
| 3 | 95° C. | 15 sec | 48 | No |
| | 60° C. | 1 min | | FAM/VIC/NED/TET |

Using the Kapa Master Mix (Kapa Biosystems):

| Stage | Temp | Time | Cycles | Data collection |
|---|---|---|---|---|
| 1 | 95° C. | 10 min | 1 | No |
| 2 | 95° C. | 15 sec | 48 | No |
| | 60° C. | 1 min | | FAM/VIC/NED/TET |

Sequences & Oligonucleotides

1. FGFR3 Mutations

The nucleotide noted in red bold is the mutated base.

The nucleotide noted in asterisk is modified by LNA technology (Locked Nucleic Acid).

For S249C Mutation (TCC→TGC)

The primers used are:

Forward F1: SEQ ID No 8 tagged in 5' with 6FAM;

Reverse R1: SEQ ID No 10 with guanine in position 19 modified by LNA technology

R248C Mutation (CGC→TGC)

The primers used are:

Forward F1: SEQ ID No 8 tagged in 5' with 6FAM;

Reverse R2: SEQ ID No 9 with cytosine in position 19 modified by LNA technology.

G372C Mutation (GGC→TGC)

The primers used are:

Forward F2: SEQ ID No 11 tagged in 5' with HEX;

Reverse R3: SEQ ID No 12 with cytosine in position 27 modified by LNA technology.

Y375C Mutation (TAT→TGT)

The primers used are:

Forward F2: SEQ ID No 1 tagged in 5' with HEX

Reverse R4: SEQ ID No 13 with cytosine in position 25 modified by LNA technology 2. TERT Mutations For detecting the specific mutation on TERT gene, one can used the following primers:

```
                                    (SEQ ID No 33)
Forward TERT: 5' CCC TTC ACC TTC CAG CTC 3' 5

                                    (SEQ ID No 34)
Reverse TERT: 5' AGC GCT GCC TGA AAC TCG 3'
```

For detecting the mutation 77C→T, by reference to SEQ ID No 32, one can used the probe

```
5' FAM/VIC-CCCGGAAGGGGCT-MGB 3'
```

For detecting the mutation 99C→T, by reference to SEQ ID No 32, one can used the probe

```
5' FAM/VIC-CCCGGAAGGGGTC-MGB 3'
```

3. Hemoglobin Subunit Beta=Housekeeping Gene

The fragment of hemoglobin subunit beta is depicted in SEQ ID No 31.

One can also use the following primers:

Forward FGLO: SEQ ID No 14; and

Reverse RGLO: SEQ ID No 15.

Quantitative Multiplex-Methylation Specific PCR

The genomic DNA is converted by bisulfite treatment.

Probe are designed such that 6FAM or VIC or TET or NED are incorporated as fluorophore (FL) in 5' end and MGB molecule are incorporated in the 3' end.

The cytosine of CpG dinucleotides which are methylated are noted in bold and are underlined.

SEPTIN 9:

SEQ ID No 3

5'TTTTTTCGTCGTTGTTTTTCGCGCGATTCGTTGTTTATTAGTTATTAT

GTCGGATTTCGCGGTTAACGCGTAGTTGGATGGGATTATTTCGGAT 3'

The inventors used SEQ ID No 16, 17 and 18 respectively as forward primer, reverse primer and probe.

SLIT2:

SEQ ID No 4

5'TAGTTTCGTCGGGTATTGGGTTTTAGATATTGCGCGGTTTTTTCGGAG

TAGTAAGTTAAAGAAAGTTTTTAGTGTCGGCGA 3'

The inventors used SEQ ID No 19, 20 and 21 respectively as forward primer, reverse primer and probe.

TWIST1:

SEQ ID No 5

5'GACGGTGTGGATGGTTTCGAGGTTTAAAAAGAAAGCGTTTAACGGTTG

GACGTATATTTCGTTAGGTTTTTTGGAAACGGTGTCGGTGTTGTAGAGT

3'

The inventors used SEQ ID No 22, 23 and 24 respectively as forward primer, reverse primer and probe.

HS3ST2:

SEQ ID No 6

5'GCGCGGGGTTATTTTAGTCGCGGAGGGCGCGTAGGTTGTTTTTCGTTT

TTACGTTTTCGTTTTTTTGTATTTATTTGTGTTATAGTTTTTTGTGTTGT

TGCGACGATTTG

The inventors used SEQ ID No 25, 26 and 27 respectively as forward primer, reverse primer and probe.

DDR1:

SEQ ID No 7

5'AGGTTTGTTTTGAGGATTTTTGAGTTTTTTTTTTTATTTTATTTCGTTG

GGAGTTTAGGGGAATTAGGGTTTGGGCGTTTGGATTTTCGGGTTTTTTAG

AACGTTTTTTAGAGAGAGGAATTGAGAGGAGAAGG3'

The inventors used SEQ ID No 28, 29 and 30 respectively as forward primer, reverse primer and probe Results FGFR3 Mutation Detection, Using AS-PCR Technology, for Identifying Patients with Bladder Cancer Detecting a mutation of FGFR3 leads to the presence of a specific peak. The amplification products were analyzed by capillary electrophoresis.

Results are shown in FIG. 2: search for S249C mutation detection in patients with cancer of the bladder (+) versus an individual without the mutation S249C (−).

The results are summarized in the table under:

TABLE 7

Detection of FGFR3 mutations

| FGFR3 MUTATION DETECTION | SENSITIVITY | SPECIFICITY |
|---|---|---|
| S249C | 27.1% (13/48) | 100% |
| Y375C | 10.5% (5/48) | (107/107) |
| G372C | 2.0% (1/48) | |
| R248C | 2.0% (1/48) | |
| All mutations | 41.6% (20/48) | |

One can see that 42% (sensitivity) of 48 patients with bladder cancer have at least one mutation. None of the controls subjects (n=107) have not shown mutations (specificity of 100%).

Efficiency and Specificity of the Quantitative Multiplex-Methylation Specific PCR (QM-MSP)

The inventors evaluated the performance of QM-MSP to quantify the methylation levels of 18 genes preselected. In order to co-amplify three methylation-specific DNA targets in real-time (triplex), we used the associations of Fam, Vie, and Ned fluorophore probes as each probe presents a strong individual spectral intensity with limited overlapping absorption spectra. We have demonstrated that our QM-MSP in mode triplex (GC1+GC2+GC3) allows co-amplification of three genes with very high amplification efficiency, close to 100% with a slope≅3, 32. The specificity of the primer pairs was assessed by sequencing of the amplicon (data not shown). This confirms the amplicon size and identity of the gene.

Validation of the Quantitative Multiplex-Methylation Specific PCR (QM-MSP) in the Urine for the Detection of Bladder Cancer The inventors evaluated each of the 18 genes preselected. An amount of about 10 ng of DNA (standard or samples) was used as a template for the QM-MSP.

The inventors selected four hypermethylated genes, those presenting the highest sensitivity and specificity, for bladder cancer detection: SEPTIN9, SLIT2, TWIST1 and HS3ST2.

QM-MSP1 quantifies, simultaneously, the degree of methylation for SEPTIN9, SLIT2, and Albumin (three genes), or SEPTIN9 and SLIT2 (two genes), or SEPTIN9 and Albumin (two genes), or SLIT2 and Albumin (two genes).

M-MSP2 quantifies, simultaneously, the degree of methylation for TWIST1, HS3ST2, and Albumin (three genes), or TWIST1 and HS3ST2 (two genes), or TWIST1 and Albumin (two genes), or HS3ST2 and Albumin (two genes).

The inventors further combined SEPTIN9, SLIT2, TWIST1 and HS3ST2. For this purpose, the inventors computed a cumulative methylation index consisting in the sum of the one, two, three, and four methylation values for each sample and used it as a varying threshold for constructing a ROC curve (Receiver Operating Characteristic). Specificities and Sensitivities are shown on Table 8 (one gene), 9 (combination of two genes), 10 (combination of three genes), and 11 (combination of four genes).

TABLEAU 8

Specificities and Sensitivities with one methylated gene

| FGFR3 mutation | 1 methylated target | Sensitivity | Specificity | Application |
|---|---|---|---|---|
| – | HS3ST2 | 67 | >90 | Screening |
| | | 52 | >97 | |
| | | 48 | 100 | |
| | SEPTIN9 | 71 | >90 | |
| | | 58 | >97 | |
| | | 38 | 100 | |
| | SLIT2 | 74 | >90 | |
| | | 71 | >97 | |
| | | 61 | 100 | |
| | TWIST1 | 71 | >90 | |
| | | 71 | >97 | |
| | | 58 | 100 | |

TABLEAU 8-continued

Specificities and Sensitivities with one methylated gene

| FGFR3 mutation | 1 methylated target | Sensitivity | Specificity | Application |
|---|---|---|---|---|
| | HS3ST2 | 78* | 74 | Surveillance & Diagnosis |
| | SEPTIN9 | 90* | 62 | |
| | SLIT2 | 87* | 41 | |
| | TWIST1 | 71* | 97 | |

*Maximum of sensitivity

TABLE 9

Specificities and Sensitivities with two methylated genes

| FGFR3 mutation | Combination of 2 methylated targets | Sensitivity | Specificity | Application |
|---|---|---|---|---|
| – | HS3ST2 + SEPTIN9 | 73 | >90 | Screening |
| | | 63 | >97 | |
| | | 46 | 100 | |
| | HS3ST2 + SLIT2 | 50 | >90 | |
| | | 46 | >97 | |
| | | 44 | 100 | |
| | HS3ST2 + TWIST1 | 52 | >90 | |
| | | 46 | >97 | |
| | | 38 | 100 | |
| | SEPTIN9 + SLIT2 | 73 | >90 | |
| | | 65 | >97 | |
| | | 54 | 100 | |
| | SEPTIN9 + TWIST1 | 73 | >90 | |
| | | 65 | >97 | |
| | | 42 | 100 | |
| | SLIT2 + TWIST1 | 48 | >90 | |
| | | 46 | >97 | |
| | | 40 | 100 | |
| | HS3ST2 + SEPTIN9 | >90 | 62 | Surveillance & Diagnosis |
| | | 94* | 60 | |
| | HS3ST2 + SLIT2 | 56* | 34 | |
| | HS3ST2 + TWIST1 | 54* | 90 | |
| | SEPTIN9 + SLIT2 | >90 | 55 | |
| | | 94* | 49 | |
| | SEPTIN9 + TWIST1 | 90* | 62 | |
| | SLIT2 + TWIST1 | 56* | 40 | |

*Maximum of sensitivity

TABLE 10

Specificities and Sensitivities with three methylated genes

| FGFR3 mutation | Combination of 3 methylated targets | Sensitivity | Specificity | Application |
|---|---|---|---|---|
| – | SLIT2 + SEPTIN9 + HS3ST2 | 73 | >90 | Screening |
| | | 65 | >97 | |
| | | 58 | 100 | |
| | HS3ST2 + SLIT2 + TWIST1 | 81 | >90 | |
| | | 71 | >97 | |
| | | 68 | 100 | |
| | HS3ST2 + TWIST1 + SEPTIN9 | 73 | >90 | |
| | | 60 | >97 | |
| | | 48 | 100 | |
| | SEPTIN9 + SLIT2 + TWIST1 | 73 | >90 | |
| | | 65 | >97 | |
| | | 56 | 100 | |
| | SLIT2 + SEPTIN9 + HS3ST2 | >90 | 64 | Surveillance & Diagnosis |
| | | 94* | 53 | |
| | HS3ST2 + SLIT2 + TWIST1 | 87* | 34 | |
| | HS3ST2 + TWIST1 + SEPTIN9 | >90 | 62 | |
| | | 94* | 60 | |
| | SEPTIN9 + SLIT2 + TWIST1 | >90 | 55 | |
| | | 94* | 48 | |

*Maximum of sensitivity

TABLE 11

Specificities and Sensitivities with four methylated genes

| Combination of 4 methylated targets | FGFR3 mutation | Sensitivity | Specificity | Application |
|---|---|---|---|---|
| HS3ST2 + SEPTIN9 + SLIT2 + TWIST1 | − | 76 | >90 | Screening |
| | | 65 | >97 | |
| | | 61 | 100 | |
| | | >90 | 66 | Surveillance |
| | | 98* | 53 | & Diagnosis |

*Maximum of sensitivity

The Multiplex Assay: Methylation and FGFR3 Mutation Detections

With the aim of developing a test of the most sensitive and most specific, the inventors evaluated the relevance of the MSP in association with the detection of FGFR3 mutations. The test performances are given according to each application (Diagnosis, Surveillance of recurrences, and targeted screening). Specificities and Sensitivities are shown on Table 12 (one gene), 13 (combination of two genes), 14 (combination of three genes), and 15 (combination of four genes).

TABLE 12

Specificities and Sensitivities with one methylated gene in association with the detection of FGFR3 mutations

| FGFR3 mutation | 1 methylated target | Sensitivity | Specificity | Application |
|---|---|---|---|---|
| + | HS3ST2 | 85 | >90 | Screening |
| | | 74 | >97 | |
| | | 70 | 100 | |
| | SEPTIN9 | 81 | >90 | |
| | | 79 | >97 | |
| | | 69 | 100 | |
| | SLIT2 | 87 | >90 | |
| | | 84 | >97 | |
| | | 77 | 100 | |
| | TWIST1 | 81 | >90 | |
| | | 81 | >97 | |
| | | 71 | 100 | |
| | HS3ST2 | >90 | 74 | Surveillance |
| | | 93* | 74 | & Diagnosis |
| | SEPTIN9 | >90 | 63 | |
| | | 92* | 63 | |

TABLE 12-continued

Specificities and Sensitivities with one methylated gene in association with the detection of FGFR3 mutations

| FGFR3 mutation | 1 methylated target | Sensitivity | Specificity | Application |
|---|---|---|---|---|
| | SLIT2 | >90 | 87 | |
| | | 94* | 83 | |
| | TWIST1 | 81* | 98 | |

*Maximum of sensitivity

TABLE 13

Specificities and Sensitivities with two methylated genes in association with the detection of FGFR3 mutations

| FGFR3 mutatio | Combination of 2 methylated targets | Sensitivity | Specificity | Application |
|---|---|---|---|---|
| + | HS3ST2 + SEPTIN9 | 81 | >90 | Screening |
| | | 81 | >97 | |
| | | 71 | 100 | |
| | HS3ST2 + SLIT2 | 77 | >90 | |
| | | 73 | >97 | |
| | | 71 | 100 | |
| | HS3ST2 + TWIST1 | 77 | >90 | |
| | | 73 | >97 | |
| | | 67 | 100 | |
| | SEPTIN9 + SLIT2 | 81 | >90 | |
| | | 81 | >97 | |
| | | 75 | 100 | |
| | SEPTIN9 + TWIST1 | 81 | >90 | |
| | | 81 | >97 | |
| | | 71 | 100 | |
| | SLIT2 + TWIST1 | 75 | >90 | |
| | | 73 | >97 | |
| | | 69 | 100 | |
| | HS3ST2 + SEPTIN9 | >90 | 62 | Surveillance |
| | | 96* | 62 | & Diagnosis |
| | HS3ST2 + SLIT2 | 79* | 84 | |
| | HS3ST2 + TWIST1 | 79* | 90 | |
| | SEPTIN9 + SLIT2 | >90 | 61 | |
| | | 96* | 49 | |
| | SEPTIN9 + TWIST1 | >90 | 63 | |
| | | 92* | 63 | |
| | SLIT2 + TWIST1 | 79* | 80 | |

*Maximum of sensitivity

TABLE 14

Specificities and Sensitivities with three methylated genes in association with the detection of FGFR3 mutations

| FGFR3 mutatio | Combination of 3 methylated targets | Sensitivity | Specificity | Application |
|---|---|---|---|---|
| + | SLIT2 + SEPTIN9 + HS3ST2 | 81 | >90 | Screening |
| | | 81 | >97 | |
| | | 77 | 100 | |
| | HS3ST2 + SLIT2 + TWIST1 | 90 | >90 | |
| | | 84 | >97 | |
| | | 81 | 100 | |
| | HS3ST2 + TWIST1 + SEPTIN9 | 81 | >90 | |
| | | 81 | >97 | |
| | | 71 | 100 | |
| | SEPTIN9 + SLIT2 + TWIST1 | 81 | >90 | |
| | | 81 | >97 | |
| | | 77 | 100 | |
| | SLIT2 + SEPTIN9 + HS3ST2 | >90 | 66 | Surveillance |
| | | 96* | 64 | & Diagnosis |
| | HS3ST2 + SLIT2 + TWIST1 | >90 | 94 | |
| | | 94* | 82 | |

TABLE 14-continued

Specificities and Sensitivities with three methylated genes in association with the detection of FGFR3 mutations

| FGFR3 mutatio | Combination of 3 methylated targets | Sensitivity | Specificity | Application |
|---|---|---|---|---|
| | HS3ST2 + TWIST1 + SEPTIN9 | >90 | 62 | |
| | | 96* | 62 | |
| | SEPTIN9 + SLIT2 + TWIST1 | >90 | 61 | |
| | | 96* | 48 | |

*Maximum of sensitivity

TABLE 15

Specificities and Sensitivities with four methylated genes in association with the detection of FGFR3 mutations

| Combination of 4 methylated targets | FGFR3 mutation | Sensitivity | Specificity | Application |
|---|---|---|---|---|
| HS3ST2 + SEPTIN9 + SLIT2 + TWIST1 | + | 83 | >90 | Screening |
| | | 83 | >97 | |
| | | 78 | 100 | |
| | | >90 | 74 | Surveillance & Diagnosis |
| | | 98* | 64 | |

*Maximum of sensitivity

For example, the Sensitivity of 98% is obtained for Surveillance of recurrences (Follow-up) and initial diagnosis of symptomatic subjects (hematuria, urinary disorders) with a good Specificity of 64%. The Specificity of 97% is obtained for the screening (population at risk) with a high Sensitivity of 83% (FIG. 3).

The inventors demonstrated that the combination of the both assays, based on the mutation detection of FGFR3 and the quantification of degree de methylation of target genes, provides to obtain accuracy highest in term of sensitivity and specificity to bladder cancer detection (Table 16).

TABLE 16 sensitivity and specificity of the combination of the mutation detection of FGFR3 and the quantification of degree de methylation of target genes

| Combination of 4 methylated targets | FGFR3 mutation | Sensitivity | Specificity | Application |
|---|---|---|---|---|
| HS3ST2 + SEPTIN9 + SLIT2 + TWIST1 | − | 76 | >90 | Screening |
| | | 65 | >97 | |
| | | 61 | 100 | |
| | + | 83 | >90 | |
| | | 83 | >97 | |
| | | 78 | 100 | |
| | − | >90 | 66 | Surveillance & Diagnosis |
| | | 98 | 53 | |
| | + | >90 | 74 | |
| | | 98 | 64 | |

Example 3: Correlation Between Threshold Value and Specificity and Sensibility The inventors have shown that the method of the invention is useful for:

- surveillance of recurrences. i.e. the follow-up of patients already diagnosed as suffering of bladder cancer,
- initial diagnosis of bladder cancer in a patient;
- screening, i.e. identification of a population at risk of developing a bladder cancer.

Depending on the targeted use of the method of the invention, sensibility and specificity must be adjusted.

Said adjustment is actually depended on the chosen specific threshold value.

The inventors thus have shown that by changing the threshold value, sensitivity and specificity of the method of the invention is changed.

This is summarized in the table 17:

TABLE 17

Influence of the threshold value on the sensitivity and specificity of the combination of the mutation detection of FGFR3 and the quantification of degree de methylation of target genes

| Combination of 4 methylated targets | FGFR3 mutation | Threshold (CMI) | Sensitivity | Specificity | Application |
|---|---|---|---|---|---|
| HS3ST2 + SEPTIN9 + SLIT2 + TWIST1 | + | 1.39 | 91 | 70 | Screening |
| | | 1.61 | 89 | 75 | |
| | | 2.38 | 85 | 80 | |
| | | 3.53 | 85 | 85 | |
| | | 5.05 | 83 | 90 | |
| | | 10.17 | 83 | 95 | |
| | | 12.52 | 83 | 98 | |
| | | 22.27 | 78 | 100 | |
| | | 53.99 | 70 | 100 | Surveillance & Diagnosis |
| | | 16.12 | 80 | 99 | |
| | | 3.53 | 85 | 85 | |
| | | 1.59 | 90 | 74 | |
| | | 0.98 | 95 | 64 | |
| | | 0.96 | 98 | 64 | |
| | | 0.44 | 98 | 50 | |

Example 4: Alternative Technologies

The inventors further showed that alternative methods are available and efficient for implementing the method of the invention.

1. Competitive Allele-Specific TaqMan PCR (CastPCR) Technology

The Competitive Allele-Specific TaqMan PCR (CastPCR) technology, has been initially developed for the mutation detection with a high sensitivity and specificity. The inventors designed a pair of primers and probes for the measure of methylation allowing carrying out the Cast-PCR method. It is a highly specific and sensitive method of detecting and quantitating rare mutations and methylated alleles in a sample that contains large amounts of genomic DNA (gDNA), crude gDNA for mutation detection or gDNA modified by bisulfite treatment for measure of methylation.

CastPCR technology combines allele-specific TaqMan® qPCR with allele-specific MGB blockers in order to suppress non-specific amplification from wild type alleles (unmutated, unmethylated). 10 ng of gDNA are used as template for PCR. The amplification products have a size of about 100 bases. The oligo Blocker and primers final concentration should be between 100 nM and 900 nM. Probe concentration should be between 100 nM and 300) nM. The PCR solution used is preferably the TaqMan Genotyping Master Mix (Life Technologies). The reaction volume is 20 μL. The schematic of Cast-PCR is noted in FIG. 4.

The thermal-cycling profile is as follows:

| Stage | Temp | Time | Cycles | Data collection |
|---|---|---|---|---|
| 1 | 95° C. | 10 min | 1 | No |
| 2 | 92° C. | 15 sec | 5 | No |
| | 58° C. | 1 min | | No |
| 3 | 92° C. | 15 sec | 40 | No |
| | 60° C. | 1 min | | FAM/VIC/NED/TET |

2. The LNA Probe Assay (Locked Nucleic Acid)

The LNA Probe assay (Locked Nucleic Acid) was developed by Exiqonk® (Vedbaek, Denmark). LNA® changes the conformation of the helix and increases the stability of the duplex. The integration of LNA® bases into Double-Dye Oligonucleotide probes (6FAM, HEX, TET) opens up great opportunities to improve techniques requiring high affinity probes as specific as possible, like mutation or methylation detection. 10 ng of gDNA are used as template for PCR. The amplification products have a size of about 100 bases. The primers final concentration should be between 100 nM and 900 nM. Probe concentration should be between 100 nM and 300 nM. The PCR solutions used are preferably Quantitect Multiplex (Qiagen) or Kapa (Biosystems). The reaction volume is 20 μL. The schematic of LNA Probe is noted in FIG. 5.

3. Microarray Technology

Microarray technology is a powerful tool for genetic research and clinical. Briefly, it utilizes nucleic acid hybridization techniques and advancements in computing technology. Microarray is a compact device that contains the well-defined immobilized capture sequence (oligonucleotide) assembled in an addressable format (i.e Agilent, Affymetrix). The oligonucleotides are attached to a glass or plastic surface. The microarray, designed by OncoDiag, will be used to identify simultaneously the mutation points of FGFR3 and TERT gene and the CpG site with cytosine methylated of each target genes (SEPTIN9, SLIT2, TWIST1, HS3ST2, DDR1), by hybridization between the sequences on the microarray and a labeled probe (the sample of interest).

4. Other Methods

Other designs are proposed by combining the technologies. For example, 6 variants (A-F) are noted in Table 14. In particular, the inventors propose a new attractive approach by carrying out the variants C and F. Simultaneously they could detect mutations and measure the degree of methylation in one tube from converted DNA by bisulfite.

TABLE 18

Summary of the different available techniques

| Variant | Technology | Add | | Template | Application |
|---|---|---|---|---|---|
| A | LNA-Probe | ASB blocker | | gDNA | Mutation |
| B | | | | Converted | Methylation |
| C | | | | gDNA | Mutation/ Methylation |
| D | Cast-PCR | ASP primer | Mutated LNA-base | gDNA | Mutation |
| E | | | Methylated cytosine-LNA | Converted gDNA | Methylation |
| F | | | Mutated LNA-base/ Methylated cytosine-LNA | Converted gDNA | Mutation/ Methylation |

The invention claimed is:

1. A method for the treatment of non-muscle invasive bladder cancer, wherein said method comprises the steps of:

a) analyzing, in a biological sample obtained from a subject, mutations at 742C→T, 746→G, 1114G→T, and 1124A→G by reference to the nucleotide numbers of SEQ ID NO: 1; or Arg248Cys, Ser249Cys, Gly372Cys, and Tyr375Cys, by reference to the amino acid numbers of SEQ ID NO: 2, in the FGFR3 gene;

b) measuring, in the biological sample, the degree of methylation of SEPTIN 9 and HS3ST2, c) detecting at least one mutation among 742C→T, 746C→G, 1114G→T, and 1124A→G, and hypermethylation of SEPTIN 9 and HS3ST2;

d) identifying the subject having non-muscle invasive bladder cancer; and e) treating the subject having the non-muscle invasive bladder cancer with a bladder cancer treatment.

2. The method according to claim 1, wherein said bladder cancer treatment is an adjuvant therapy selected from the group consisting of radiotherapy, hormone therapy, chemotherapy, immunotherapy and monoclonal antibody therapy.

3. The method according to claim 1, wherein step b) further comprises measuring the degree of methylation of SLIT2.

4. The method according to claim 1, wherein step b) further comprises measuring the degree of methylation of TWIST 1.

5. The method according to claim 1, wherein step a) is performed by allele specific PCR (AS-PCR).

6. The method according to claim 1, wherein step b) is performed by quantitative real-time multiplex methylation specific polymerase chain reaction (Qm-PCR).

* * * * *

SEQUENCE LISTING

<160> NUMBER OF SEQ ID NOS: 36

<210> SEQ ID NO 1
<211> LENGTH: 2427
<212> TYPE: DNA
<213> ORGANISM: Homo sapiens

<400> SEQUENCE: 1
atgggcgccc ctgcctgcgc cctcgcgctc tgcgtggccg tggccatcgt ggccggcgcc 60
tcctcggagt ccttggggac ggagcagcgc gtcgtggggc gagcggcaga agtcccgggc 120
ccagagcccg gccagcagga gcagttggtc ttcggcagcg gggatgctgt ggagctgagc 180
tgtcccccgc ccgggggtgg tcccatgggg cccactgtct gggtcaagga tggcacaggg 240
ctggtgccct cggagcgtgt cctggtgggg ccccagcggc tgcaggtgct gaatgcctcc 300

-continued

```
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga atggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc   1020
accaatttca taggcgtggc cgagaaggcc ttttggctga gcgttcacgg gccccgagca   1080
gccgaggagg agctggtgga ggctgacgag gcgggcagtg tgtatgcagg catcctcagc   1140
tacggggtgg gcttcttcct gttcatcctg gtggtggcgg ctgtgacgct ctgccgcctg   1200
cgcagccccc ccaagaaagg cctgggctcc cccaccgtgc acaagatctc ccgcttcccg   1260
ctcaagcgac aggtgtccct ggagtccaac gcgtccatga gctccaacac accactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagcccctt   1440
ggggagggct gcttcggcca ggtggtcatg gcggaggcca tcggcattga caaggaccgg   1500
gccgccaagc ctgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggcccctgt acgtgctggt ggagtacgcg   1680
gccaagggta acctgcggga gtttctgcgg gcgcggcggc ccccgggcct ggactactcc   1740
ttcgacacct gcaagccgcc cgaggagcag ctcaccttca aggacctggt gtcctgtgcc   1800
taccaggtgg cccggggcat ggagtacttg gcctcccaga agtgcatcca cagggacctg   1860
gctgcccgca atgtgctggt gaccgaggac aacgtgatga agatcgcaga cttcgggctg   1920
gcccgggacg tgcacaacct cgactactac aagaagacaa ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg gctccccgta ccccggcatc   2100
cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca agcagctggt ggaggacctg gaccgtgtcc ttaccgtgac gtccaccgac   2280
gagtacctgg acctgtcggc gcctttcgag cagtactccc cgggtggcca ggacaccccc   2340
agctccagct cctcagggga cgactccgtg tttgcccacg acctgctgcc cccggcccca   2400
cccagcagtg gggctcgcg gacgtga                                       2427
```

<210> SEQ ID NO 2
<211> LENGTH: 808
<212> TYPE: PRT
<213> ORGANISM: Homo sapiens

<400> SEQUENCE: 2

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415
```

```
Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
    690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
    770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805
```

<210> SEQ ID NO 3
<211> LENGTH: 94

-continued

<212> TYPE: DNA
<213> ORGANISM: Homo sapiens

<400> SEQUENCE: 3 tttttcgtc gttgtttttc gcgcgattcg ttgtttatta gttattatgt cggatttcgc 60
ggttaacgcg tagttggatg ggattatttc ggat 94

<210> SEQ ID NO 4
<211> LENGTH: 81
<212> TYPE: DNA
<213> ORGANISM: Homo sapiens

<400> SEQUENCE: 4
tagtttcgtc gggtattggg ttttagatat tgcgcggttt tttcggagta gtaagttaaa 60
gaaagttttt agtgtcggcg a 81

<210> SEQ ID NO 5
<211> LENGTH: 97
<212> TYPE: DNA
<213> ORGANISM: Homo sapiens

<400> SEQUENCE: 5
gacggtgtgg atggtttcga ggtttaaaaa gaaagcgttt aacggttgga cgtatatttc 60
gttaggtttt ttggaaacgg tgtcggtgtt gtagagt 97

<210> SEQ ID NO 6
<211> LENGTH: 110
<212> TYPE: DNA
<213> ORGANISM: Homo sapiens

<400> SEQUENCE: 6
gcgcggggtt attttagtcg cggagggcgc gtaggttgtt tttcgttttt acgttttcgt 60
ttttttgtat ttatttgtgt tatagttttt tgtgttgttg cgacgatttg 110

<210> SEQ ID NO 7
<211> LENGTH: 133
<212> TYPE: DNA
<213> ORGANISM: Homo sapiens

<400> SEQUENCE: 7
aggtttgttt tgaggatttt tgagtttttt ttttatttta tttcgttggg agtttagggg 60
aattagggtt tgggcgtttg gattttcggg ttttttagaa cgttttttag agagaggaat 120
tgagaggaga agg 133

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
cagtggcggt ggtggtgagg 20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
atgggccggt gcggggagca 20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
caggatgggc cggtgcgggc 20

<210> SEQ ID NO 11
<211> LENGTH: 23
<212> TYPE: DNA
<213> ORGANISM: Artificial
<220> FEATURE:
<223> OTHER INFORMATION: primer

<400> SEQUENCE: 11
atgtctttgc agccgaggag gag 23

<210> SEQ ID NO 12
<211> LENGTH: 28
<212> TYPE: DNA
<213> ORGANISM: Artificial
<220> FEATURE:
<223> OTHER INFORMATION: primer

<400> SEQUENCE: 12
agctgaggat gcctgcatac acactgca 28

<210> SEQ ID NO 13
<211> LENGTH: 25
<212> TYPE: DNA
<213> ORGANISM: Artificial
<220> FEATURE:
<223> OTHER INFORMATION: primer

<400> SEQUENCE: 13
accccgtagc tgaggatgcc tgctc 25

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
cctttgggga tctgtccact cctga 25

<210> SEQ ID NO 15
<211> LENGTH: 23
<212> TYPE: DNA
<213> ORGANISM: Artificial
<220> FEATURE:
<223> OTHER INFORMATION: primer

<400> SEQUENCE: 15
gttgtccagg tgagccaggc cat 23

<210> SEQ ID NO 16
<211> LENGTH: 22

-continued

<212> TYPE: DNA
<213> ORGANISM: Artificial
<220> FEATURE:
<223> OTHER INFORMATION: primer

<400> SEQUENCE: 16 tttttcgtc gttgttttc gc 22

<210> SEQ ID NO 17
<211> LENGTH: 25
<212> TYPE: DNA
<213> ORGANISM: Artificial
<220> FEATURE:
<223> OTHER INFORMATION: primer

<400> SEQUENCE: 17
atccgaaata atcccatcca actac 25

<210> SEQ ID NO 18
<211> LENGTH: 17
<212> TYPE: DNA
<213> ORGANISM: Artificial
<220> FEATURE:
<223> OTHER INFORMATION: probe

<400> SEQUENCE: 18
attatgtcgg atttcgc 17

<210> SEQ ID NO 19
<211> LENGTH: 23
<212> TYPE: DNA
<213> ORGANISM: Artificial
<220> FEATURE:
<223> OTHER INFORMATION: primer

<400> SEQUENCE: 19
tagtttcgtc gggtattggg ttt 23

<210> SEQ ID NO 20
<211> LENGTH: 26
<212> TYPE: DNA
<213> ORGANISM: Artificial
<220> FEATURE:
<223> OTHER INFORMATION: primer

<400> SEQUENCE: 20
tcgccgacac taaaaacttt ctttaa 26

<210> SEQ ID NO 21
<211> LENGTH: 17
<212> TYPE: DNA
<213> ORGANISM: Artificial
<220> FEATURE:
<223> OTHER INFORMATION: probe

<400> SEQUENCE: 21
agatattgcg cggtttt 17

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22

-continued gacggtgtgg atggtttcga 20

<210> SEQ ID NO 23
<211> LENGTH: 24
<212> TYPE: DNA
<213> ORGANISM: Artificial
<220> FEATURE:
<223> OTHER INFORMATION: primer

<400> SEQUENCE: 23
actctacaac accgacaccg tttc 24

<210> SEQ ID NO 24
<211> LENGTH: 18
<212> TYPE: DNA
<213> ORGANISM: Artificial
<220> FEATURE:
<223> OTHER INFORMATION: probel

<400> SEQUENCE: 24
agcgtttaac ggttggac 18

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
gcgcggggtt attttagtcg 20

<210> SEQ ID NO 26
<211> LENGTH: 22
<212> TYPE: DNA
<213> ORGANISM: Artificial
<220> FEATURE:
<223> OTHER INFORMATION: primer

<400> SEQUENCE: 26
caaatcgtcg caacaacaca aa 22

<210> SEQ ID NO 27
<211> LENGTH: 19
<212> TYPE: DNA
<213> ORGANISM: Artificial
<220> FEATURE:
<223> OTHER INFORMATION: primer

<400> SEQUENCE: 27
cgtaaaaacg aaaaacaac 19

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28
aggtttgttt tgaggatttt tgagttt 27

<210> SEQ ID NO 29
<211> LENGTH: 27
<212> TYPE: DNA
<213> ORGANISM: Artificial

-continued

<220> FEATURE:
<223> OTHER INFORMATION: primer

<400> SEQUENCE: 29
ccttctcctc tcaattcctc tctctaa 27

<210> SEQ ID NO 30
<211> LENGTH: 19
<212> TYPE: DNA
<213> ORGANISM: Artificial
<220> FEATURE:
<223> OTHER INFORMATION: probe

<400> SEQUENCE: 30
cgtttggatt ttcgggttt 19

<210> SEQ ID NO 31
<211> LENGTH: 110
<212> TYPE: DNA
<213> ORGANISM: Homo sapiens

<400> SEQUENCE: 31
cctttgggga tctgtccact cctgatgctg ttatgggcaa ccctaaggtg aaggctcatg 60
gcaagaaagt gctcggtgcc tttagtgatg gcctggctca cctggacaac 110

<210> SEQ ID NO 32
<211> LENGTH: 155
<212> TYPE: DNA
<213> ORGANISM: Homo sapiens

<400> SEQUENCE: 32
tcgcgacgga ctttgagcgc ggcgctcctc tcccgccccg gcgcctttcc ttcccctccc 60
cgaccctccc gggcctcccc cgacccggcc cctgggccct ccccagccct gccccgcccc 120
aggcgcgcct cctccgcctc gaccttccac ttccc 155

<210> SEQ ID NO 33
<211> LENGTH: 18
<212> TYPE: DNA
<213> ORGANISM: Artificial
<220> FEATURE:
<223> OTHER INFORMATION: primer forward

<400> SEQUENCE: 33
cccttcacct tccagctc 18

<210> SEQ ID NO 34
<211> LENGTH: 18
<212> TYPE: DNA
<213> ORGANISM: Artificial
<220> FEATURE:
<223> OTHER INFORMATION: reverse primer

<400> SEQUENCE: 34
agcgctgcct gaaactcg 18

<210> SEQ ID NO 35
<211> LENGTH: 13
<212> TYPE: DNA
<213> ORGANISM: Artificial
<220> FEATURE:
<223> OTHER INFORMATION: Probe mutation 77CT of TERT

<400> SEQUENCE: 35

-continued

```
cccggaaggg gct                                                        13


<210> SEQ ID NO 36
<211> LENGTH: 13
<212> TYPE: DNA
<213> ORGANISM: Artificial
<220> FEATURE:
<223> OTHER INFORMATION: probe mutation 99CT of TERT

<400> SEQUENCE: 36

cccggaaggg gtc                                                        13
```